(12) United States Patent
Schotz et al.

(10) Patent No.: US 9,261,510 B2
(45) Date of Patent: Feb. 16, 2016

(54) DETECTION OF PRIMARY INFECTIONS WITH PATHOGENS

(75) Inventors: Christian Schotz, Penzberg (GB); Elke Faatz, Huglfing (GB); Peter Schaarschmidt, Uffing (GB); Urban Schmitt, Oberhausen (GB)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1009 days.

(21) Appl. No.: 12/104,751

(22) Filed: Apr. 17, 2008

(65) Prior Publication Data
US 2009/0042212 A1 Feb. 12, 2009

(30) Foreign Application Priority Data
Apr. 20, 2007 (EP) ..................................... 07008124

(51) Int. Cl.
| | | |
|---|---|---|
| C07K 14/20 | (2006.01) | |
| C07K 14/245 | (2006.01) | |
| C07K 14/45 | (2006.01) | |
| C07K 14/47 | (2006.01) | |
| C12N 15/62 | (2006.01) | |
| G01N 33/68 | (2006.01) | |

(52) U.S. Cl.
CPC ............ *G01N 33/6854* (2013.01); *C07K 14/20* (2013.01); *C07K 14/245* (2013.01); *C07K 14/45* (2013.01); *C07K 14/47* (2013.01); *C12N 15/62* (2013.01); *C07K 2319/70* (2013.01); *C12N 2710/16122* (2013.01); *C12N 2710/16134* (2013.01); *G01N 2333/02* (2013.01); *G01N 2333/035* (2013.01); *G01N 2333/04* (2013.01); *G01N 2333/045* (2013.01); *G01N 2333/05* (2013.01); *G01N 2333/19* (2013.01); *G01N 2333/45* (2013.01)

(58) Field of Classification Search
None
See application file for complete search history.

(56) References Cited

U.S. PATENT DOCUMENTS

| | | |
|---|---|---|
| 6,207,420 B1 | 3/2001 | Harrison et al. |
| 6,489,129 B1 | 12/2002 | Faatz et al. |
| 6,645,732 B2 | 11/2003 | Faatz et al. |

FOREIGN PATENT DOCUMENTS

| | | | |
|---|---|---|---|
| DE | 19919121 A1 | 11/2000 | |
| EP | 1090994 A2 | 4/2001 | |
| EP | 1522585 A1 | 4/2005 | |
| EP | 1780282 A1 | 5/2007 | |
| WO | 96/03652 A1 | 2/1996 | |
| WO | 98/23955 A3 | 6/1998 | |
| WO | 98/23961 A1 | 6/1998 | |
| WO | WO 03/051305 | * | 12/2002 |
| WO | 03/000878 A3 | 1/2003 | |
| WO | 2004/053091 A2 | 6/2004 | |
| WO | WO 2006/078273 | * | 7/2006 |

OTHER PUBLICATIONS

Kropff et al., An ELISA using recombinant proteins for the detection of neutralizing antibodies against human cytomegalovirus, 1993, Journal of Medical Virology, vol. 39, No. 3, abstract.*
Ohlin et al., Cytomegalovirus Glycoprotein B-Specific Antibody Analysis Using Electrochemiluminescence Detection-Based Techniques, 1997, Clinical and Diagnostic Laboratory Immunology, vol. 4, No. 1, pp. 107-111.*
Hekker et al., Indirect Immunofluorescence Test for Detection of IgM Antibodies to Cytomegalovirus, 1979, Journal of Infectious Diseases, vol. 140, No. 4, pp. 596-600.*
Weber et al., Screening of blood donors for human cytomegalovirus (HCMV) IgG antibody with an enzyme immunoassay using recombinant antigens, 1999, Journal of Clinical Virology, vol. 14, pp. 173-181.*
Aubert, D. et al., "Recombinant Antigens to Detect Toxoplasma gondii-Specific Immonuglobulin G and Immunoglobulin M in Human Sera by Enzyme Immunoassay," Journal of Clinical Mircrobiology, Mar. 2000, pp. 1144-1150, vol. 38, No. 3.
Carlos, Maria P. et al., "Humoral immunity to immunodominant epitopes of Hepatitis C virus in individuals infeted with genotypes 1a or 1b," Clinical Immunology, 2004, pp. 22-27, vol. 111.
Chatterjee, Deb K. and Esposito, Dominic, "Enhanced soluble protein expression using two new fusion tags," Protein Expression and Purification, 2006, pp. 122-129, vol. 46.
Colucci, G. et al., "Identification of a Major Hepatitis B Core Antigen (HBcAg) Determinant by Using Synthetic Peptides and Monoclonal Antibodies," The Journal of Immunology, Dec. 15, 1988, pp. 4376-4380, vol. 141, No. 12.
Eggers, Maren et al., "Use of Recombinant Glycoprotein Antigens gB and gH for Diagnosis of Primary Human Cytomegalovirus Infection During Pregnancy," Journal of Medical Virology, 2001, pp. 135-142, vol. 63.
Ehrnsperger, Monika et al., "Stabilization of Proteins and Peptides in Diagnostic Immunological Assays by the Molecular Chaperone Hsp25," Analytical Biochemistry, 1998, pp. 218-225, vol. 259.
Green, Kim Y. and Dorsett, Preston H., "Rubella Virus Antigens: Localization of Epitopes Involved in Hemagglutination and Neutralization by Using Monoclonal Antibodies," Journal of Virology, Mar. 1986, pp. 893-898, vol. 57, No. 3.
Greijer, Astrid E. et al., "Molecular Fine-Specificity Analysis of Antibody Response to Human Cytomegalovirus and Design of Novel Synthetic-Peptide-Based Serodiagnostic Assay," Journal of Clinical Microbiology, Jan. 1999, pp. 179-188, vol. 37, No. 1.
Lee, Cameron C. et al., "Designing dendrimers for biological applications," Nature Biotechnology, Dec. 2005, pp. 1517-1526, vol. 23, No. 12.

(Continued)

*Primary Examiner* — Benjamin P Blumel
(74) *Attorney, Agent, or Firm* — Stinson Leonard Street LLP

(57) ABSTRACT

The present invention relates to fusion proteins suitable as test antigens in the detection of infections with pathogens, particularly of primary infections with pathogens. Further, the invention relates to methods for detecting and differentially determining antibodies, particularly IgM antibodies resulting from an infection with a pathogenic organism. Furthermore, test reagents for carrying out these methods are provided.

22 Claims, 3 Drawing Sheets

(56) References Cited

OTHER PUBLICATIONS

Liang, Fang Ting et al., "Analysis of Antibody Response to Invariable Regions of VlsE, the Variable Surface Antigen of Borrelia burgdorferi," Infection and Immunity, Dec. 1999, pp. 6702-6706, vol. 67, No. 12.

Liang, Fang Ting et al., "An Immunodominant Conserved Region Within the Variable Domain of VlsE, the Variable Surface Antigen of Borrelia bergdorferi," Journal of Immunology, 1999, pp. 5566-5573, vol. 163.

Liang, Fang Ting et al., "Sensitive and Specific Serodiagnosis of Lyme Disease by Enzyme-Linked Immunosorbent Assay with a Peptide Based on an Immunodominant Conserved Region of Borrelia bergdorferi VlsE," Journal of Clinical Microbiology, Dec. 1999, pp. 3990-3996, vol. 37, No. 12.

Liljeqvist, Jan-Ake et al., "Localization of type-specific epitopes of herpes simplex virus type 2 glycoprotein G recognized by human and mouse antibodies," Journal of General Virology, 1998, pp. 1215-1224, vol. 79.

Marsden, H. S. et al., "Identification of an Immunodominant Sequential Epitope in Glycoprotein G of Herpes Simplex Virus Type 2 That Is Useful for Serotype-Specific Diagnosis," Journal of Medical Virology, 1998, pp. 79-84, vol. 56.

McCarthy, Micheline et al., "Immunodominant T-Cell Epitopes of Rubella Virus Structural Proteins Defined by Synthetic Peptides," Journal of Virology, Feb. 1993, pp. 673-681, vol. 67, No. 2.

Mitchell, Leslie Ann et al., "Characterization of Rubell Virus-Specific Antibody Response by Using a New Synthetic Peptide-Based Enzyme-Linkied Immunosorbent Assay," Journal of Clinical Microbiology, Jul. 1992, pp. 1841-1847, vol. 30, No. 7.

Oscherwitz, Jon et al., "A V3 loop haptenic peptide sequence, when tandemly repeated, enhances immunogenicity by facilitating helper T-cell responses to a covalently linked carrier protein," Vaccine, 1999, pp. 2392-2399, vol. 17.

Pace, C. Nick et al., "How to measure and predict the molar absortion coefficient of a protein," Protein Science, 1995, pp. 2411-2423. vol. 4.

Pfrepper, Klaus-Ingmar et al., "Seroreactivity to and Avidity for Recombinant Antigens in Toxoplasmosis," Clinical and Diagnostic Laboratory Immunology, Aug. 2005, pp. 977-982, vol. 12, No. 8.

Salfeld, J. et al., "Antigenic Determinants and Functional Domains in Core Antigen and e Antigen from Hepatitis B Virus," Journal of Virology, Feb. 1989, pp. 798-808, vol. 63, No. 2.

Samuel, Dhanraj et al., "High Level Expression of Recombinant Mumps Nucleoprotein in *Saccharomyces cerevisiae* and Its Evaluation in Mumps IgM Serology," Journal of Medical Virology, 2002, pp. 123-130, vol. 66.

Schagger, Hermann et al., "Tricine-Sodium Dodecyl Sulfate-Polyacrylamide Gel Electrophoresis for the Separation of Proteins in the Range from 1 to 100 kDa," Analytical Biochemistry, 1987, pp. 368-379, vol. 166.

Scholz, Christian et al., "Functional Solubilization of Aggregation-prone HIV Envelope Proteins by Covalent Fusion with Chaperone Modules," Journal of Molecular Biology, 2005, pp. 1229-1241, vol. 345.

Scholz, Christian. et al., "SlyD Proteins from Different Species Exhibit High Prolyl Isomerase and Chaperone Activities," Biochemistry, 2006, pp. 20-33, vol. 45.

Schoppel, K. et al., The Humoral Immune Response against Human Cytomegalovirus Is Characterized by a Delayed Synthesis of Glycoprotein-Specific Antibodies, The Journal of Infectious Diseases, 1997, pp. 533-544, vol. 175.

Tam, James P., "Recent advances in multiple antigen peptides," Journal of Immunological Methods, 1996, pp. 17-32, vol. 196.

Terry, G. M. et al., "Localization of the rubella E1 epitopes," Archives of Virology, 1988, pp. 189-197, vol. 98.

Tunback, Petra et al., "Glycoprotein G of herpes simplex virus type 1: identification of type-specific epitopes by human antibodies," Journal of General Virology, 2000, pp. 1033-1040, vol. 81.

Wolinsky, Jerry S. et al., "Monoclonal Antibody-Defined Epitope Map of Expressed Rubella Virus Protein Domains," Journal of Virology, Aug. 1991, pp. 3986-3994, vol. 65, No. 8.

Yang, Xinzhen et al., Characterization of Stable, Soluble Trimers Containing Comlete Ectodomains of Human Immunodeficiency Virus Type 1 Envelope Glycoproteins,: Journal of Virology, Jun. 2000, pp. 5716-5725, vol. 74, No. 12.

Zvirbliene, A. et al.,"Mapping of B cell epitopes in measles virus nucleocaspid protein," Archives of Virology, 2007, pp. 25-39, vol. 152.

* cited by examiner

Figure 2

SEQ ID NO: 1 SlyD (1-165)

```
  1 MKVAKDLVVS LAYQVRTEDG VLVDESPVSA PLDYLHGHGS LISGLETALE GHEVGDKFDV   60
 61 AVGANDAYGQ YDENLVQRVP KDVFMGVDEL QVGMRFLAET DQGPVPVEIT AVEDDHVVVD  120
121 GNHMLAGQNL KFNVEVVAIR EATEEELAHG HVHGAHDHHH DHDHD
```

SEQ ID NO: 2 FkpA (26-270)

```
  1                 AEAAK PATAADSKAA FKNDDQKSAY ALGASLGRYM   60
 61 ENSLKEQEKL GIKLDKDQLI AGVQDAFADK SKLSDQEIEQ TLQAFEARVK SSAQAKMEKD  120
121 AADNEAKGKE YREKFAKEKG VKTSSTGLVY QVVEAGKGEA PKDSDTVVVN YKGTLIDGKE  180
181 FDNSYTRGEP LSFRLDGVIP GWTEGLKNIK KGGKIKLVIP PELAYGKAGV PGIPPNSTLV  240
241 FDVELLDVKP APKADAKPEA DAKAADSAKK
```

SEQ ID NO: 3 Skp (21-161)

```
  1                 ADKIAIVNMG SLFQQVAQKT GVSNTLENEF KGRASELQRM   60
 61 ETDLQAKMKK LQSMKAGSDR TKLEKDVMAQ RQTFAQKAQA FEQDRARRSN EERGKLVTRI  120
121 QTAVKSVANS QDIDLVVDAN AVAYNSSDVK DITADVLKQV K
```

SEQ ID NO: 4 Skp-ppUL32-X1 (ppUL32= pp150, 587-640)

```
M A D K I A I V N M G S L F Q Q V A Q K T G V S N T L E N E F R G R A S E L Q
R M E T D L Q A K M K K L Q S M K A G S D R T K L E K D V M A Q R Q T F A Q K
A Q A F E Q D R A R R S N E E R G K L V T R I Q T A V K S V A N S Q D I D L V
V D A N A V A Y N S S D V K D I T A D V L K Q V K G G G S G G G S G G G S G G
G S G G G S G G G A G A G A A I L T P T P V N P S T A P A P A P T P T F A G T
Q T P V N G N S P W A P T A P L P G D M N P A N G G G L E H H H H H H
```

SEQ ID NO: 5 Skp-ppUL32-X4 (ppUL32=pp150, 587-640)

SEQ ID NO: 6 Skp-pp150-X1 (pp150 999-1048)

```
M A D K I A I V N M G S L F Q Q V A Q K T G V S N T L E N E F R G R A S E L Q
R M E T D L Q A K M K K L Q S M K A G S D R T K L E K D V M A Q R Q T F A Q K
A Q A F E Q D R A R R S N E E R G K L V T R I Q T A V K S V A N S Q D I D L V
V D A N A V A Y N S S D V K D I T A D V L K Q V K G G G S G G G S G G G S G G
G S G G G S G G G M K T V A F D L S S P Q K S G T G P Q P G S A G M G G A K T
P S D A V Q N I L Q K I E K I K N T E E G G G L E H H H H H H
```

SEQ ID NO: 7 Skp-pp150-X4 (pp150 999-1048)

```
M A D K I A I V N M G S L F Q Q V A Q K T G V S N T L E N E F R G R A S E L Q
R M E T D L Q A K M K K L Q S M K A G S D R T K L E K D V M A Q R Q T F A Q K
A Q A F E Q D R A R R S N E E R G K L V T R I Q T A V K S V A N S Q D I D L V
V D A N A V A Y N S S D V K D I T A D V L K Q V K G G G S G G G S G G G S G G
G S G G G S G G G M K T V A F D L S S P Q K S G T G P Q P G S A G M G G A K T
P S D A V Q N I L Q K I E K I K N T E E G G M K T V A F D L S S P Q K S G T
G P Q P G S A G M G G A K T P S D A V Q N I L Q K I E K I K N T E E G G G M K
T V A F D L S S P Q K S G T G P Q P G S A G M G G A K T P S D A V Q N I L Q K
I E K I K N T E E G G M K T V A F D L S S P Q K S G T G P Q P G S A G M G G
A K T P S D A V Q N I L Q K I E K I K N T E E G G G L E H H H H H H
```

SEQ ID NO: 8 Skp-p52-X1 (p52 254-293)

```
M A D K I A I V N M G S L F Q Q V A Q K T G V S N T L E N E F R G R A S E L Q
R M E T D L Q A K M K K L Q S M K A G S D R T K L E K D V M A Q R Q T F A Q K
A Q A F E Q D R A R R S N E E R G K L V T R I Q T A V K S V A N S Q D I D L V
V D A N A V A Y N S S D V K D I T A D V L K Q V K G G G S G G G S G G G S G G
G S G G G S G G V A S R N G L F A V E N F L T E E P F Q R G D P F D K N Y V
G N S G K S R G G G G G L E H H H H H H
```

SEQ ID NO: 9 Skp-p52-X4 (p52 254-293)

```
M A D K I A I V N M G S L F Q Q V A Q K T G V S N T L E N E F R G R A S E L Q
R M E T D L Q A K M K K L Q S M K A G S D R T K L E K D V M A Q R Q T F A Q K
A Q A F E Q D R A R R S N E E R G K L V T R I Q T A V K S V A N S Q D I D L V
V D A N A V A Y N S S D V K D I T A D V L K Q V K G G G S G G G S G G G S G G
G S G G G S G G V A S R N G L F A V E N F L T E E P F Q R G D P F D K N Y V
G N S G K S R G G G G G V A S R N G L F A V E N F L T E E P F Q R G D P F D
K N Y V G N S G K S R G G G G G V A S R N G L F A V E N F L T E E P F Q R G
D P F D K N Y V G N S G K S R G G G G G V A S R N G L F A V E N F L T E E P
F Q R G D P F D K N Y V G N S G K S R G G G G G L E H H H H H H
```

DETECTION OF PRIMARY INFECTIONS WITH PATHOGENS

RELATED APPLICATIONS

This application claims priority to European application EP 07008124.5 filed Apr. 20, 2007.

FIELD OF THE INVENTION

The present invention relates to fusion polypeptides suitable as test antigens in the detection of infections with pathogens, particularly of primary infections with pathogens. Further, the invention refers to methods for detecting and differentially determining IgM antibodies resulting from an infection with a pathogen. Furthermore, test reagents for carrying out these methods are provided.

BACKGROUND

Apart from the PCR technology, immunological tests still play a major role in infection serology. By the specific determination of different-immunoglobulin classes, immunology makes it possible to analyze the stage of a disease. By determining IgM and IgG titers against certain viral antigens it becomes possible to distinguish between different infection stages, e.g., acute infections, recurrent infections, chronic/persistent infections or post-infectious disease stages. For instance, IgG molecules against the viral glycoproteins are only generated at a late stage of an infection, with cytomegalovirus (Schoppel et al. JID (1997) 175, 533-544; Eggers et al., J. Med. Virol. (2001) 63, 135-142).

A crucial aspect of a reliable specific detection of IgG and IgM in the presence of the respective other immunoglobulin class is the effective epitope concentration or effective epitope density of the detection antigen. A high effective epitope concentration means that there is a high epitope density and all epitopes are accessible for antibody binding. In contrast to this, also polypeptide aggregates have a high epitope concentration, but the effective epitope concentration is low because the epitopes are partially or completely buried or hidden and thus not accessible for antibody binding. High epitope concentrations are a precondition for specific IgM recognition whereas low epitope concentrations are a precondition for the specific recognition of IgG. In a classic sandwich IgM test, which shall detect IgM molecules against the antigen A, a multimeric antigen A is used as an immobilized capture antigen. The same multimeric antigen A carrying a reporter group is used as a detection antigen. The IgM analyte binds to the capture antigen and the detection antigen whereby the reporter group is immobilized on a solid phase (e.g., beads coated with streptavidin). In order to avoid interferences of IgG molecules directed against A, an unlabelled monomeric antigen A is added as an interference elimination agent to the test (WO 98/23955, U.S. Pat. No. 6,489,129 B1). Correspondingly, a specific IgG sandwich test (WO 98/23961, U.S. Pat. No. 6,645,732 B1) may comprise a monomeric antigen for the detection of IgG and an unlabelled multimeric antigen to avoid interferences with IgM.

The principle which allows a specific detection of IgM and IgG molecules is based on their respective molecular structures. The pentameric IgM has ten identical paratopes for antigen binding whereas the monomeric IgG has only two binding sites per molecule. The detection of IgG is based on the affinity to the analyte whereas the detection of IgM is based on the avidity. In the first case, the binding is achieved by a high affinity interaction between epitope and paratope (i.e., IgG antigen binding site); in the latter case it is achieved by a cooperative enhancement of several low affinity interactions (avidity means that the single dissociation constants are not added but multiplied, i.e., a relatively weak interaction with a kD of ~10-5 M is increased by two independent binding events to yield a high affinity interaction with a kD of ~10-10 M). Thus, it can be said as a rule of thumb that monomeric antigens are used for the detection of IgG and oligomeric/multimeric antigens are used for the detection of IgM.

Antigen oligomerization or multimerization may be achieved by chemical crosslinking of monomeric antigens by homo- or heterobifunctional crosslinkers. Generally, the oligo- or multimerization may be optimized by adjusting the reaction conditions (concentration of protein and crosslinker, pH, temperature, agitation rate, reaction time), which is very time-consuming and labor-intensive. Nevertheless, different degrees of crosslinking may be obtained in different batches, which require subsequent fractionation and/or calibration procedures. Further, higher degree of crosslinking normally leads to a reduction of solubility, which may lead to problems in the test performance. It is thus desired to find an improved method to provide multimeric antigens in a defined and reproducible manner.

U.S. Pat. No. 6,207,420 describes a fusion sequence comprising a carrier protein comprising an *E. coli* protein having a predicted solubility probability of at least 90% fused to a target heterologous peptide or protein. Preferably, the heterologous peptide or protein is normally insoluble when expressed in bacteria.

WO 03/000878 describes a fusion protein comprising at least one target polypeptide and upstream thereto at least one FKBP chaperone, which is selected from the group consisting, of FkpA, SlyD and trigger factor. The target polypeptide may be a mammalian gene product or a gene product of a mammalian pathogen.

BRIEF DESCRIPTION OF THE FIGURES

FIG. 2: Amino acid sequences for SEQ ID NOs 1-5
FIG. 3: Amino acid sequences for SEQ ID NOs 6-9

DESCRIPTION OF THE INVENTION

Figure 1:
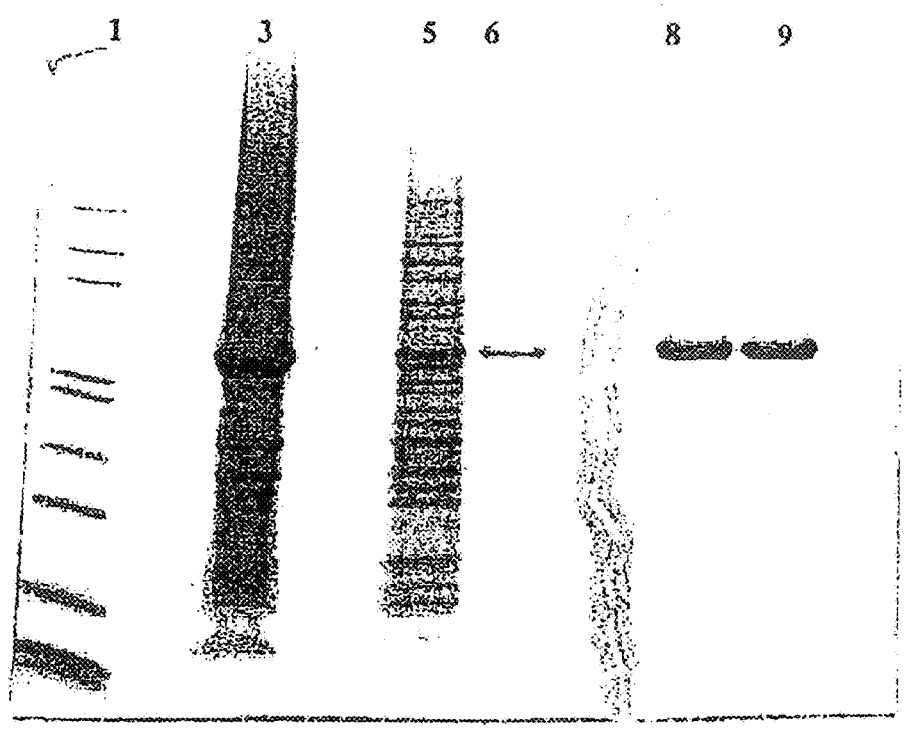
FIG. 1: Purification of Skp-p52-X4 as documented by SDS-PAGE. Lane 1, protein standard Mark 12 Unstained from Invitrogen; lane 3, chaotropic crude lysate of the overproducing *E. coli* strain BL21/DE 3; lane 5, IMAC flowthrough; lane 6, imidazole wash fraction, lane 8, imidazole elution fraction; lane 9, Skp-p52-X4 after gel filtration (SUPERDEX 200, GE Healthcare Bio-Sciences AB). Skp-p52-X4 can be purified and refolded with high yields in the simple one-step protocol described in the Methods.

A first aspect of the invention refers to a fusion polypeptide comprising at least one multimerization domain and a plurality of copies of an epitope segment from a pathogen.

The fusion polypeptide molecules are capable of forming a multimer. A multimer comprises a plurality of monomeric subunits associated by non-covalent interactions via the multimerization domain. The multimer may be formed by, e.g., incubating fusion polypeptide molecules under suitable conditions.

The fusion polypeptides of the present invention are genetic fusions which can be produced in high amounts and reproducible quality according to standard methods. The fusion polypeptides and the multimers formed therefrom have a high stability and solubility and thus are excellent test antigens in methods for detecting antibodies resulting from an infection with a pathogen. Preferably, the fusion polypeptides are used in a determination of IgM antibodies, more preferably in a differential determination of IgM antibodies, most preferably in a differential determination of early IgM antibodies which occur in an acute and/or primary infection. The fusion polypeptides may carry reporter groups and/or capture groups and thus may be used as detection and/or capturing antigens. Further, the fusion polypeptides are also suitable as interference elimination agents.

The fusion polypeptide molecules of the present invention preferably comprise one or two multimerization domains, more preferably one multimerization domain. The multimerization domain is preferably located at the N- and/or C-terminus of the fusion polypeptide, more preferably at the N-terminus. The multimerization domain is a polypeptide sequence which supports multimerization of individual fusion polypeptide molecules, wherein a multimer is formed which is comprised of a plurality of monomeric subunits, which are associated by non-covalent interactions. The monomeric subunits of the complex are genetic fusion proteins, wherein the individual amino acid residues are linked by peptide bonds. The monomeric subunits of the multimer are preferably identical.

For example, the multimerization domain may be a dimerization domain, i.e., a domain which supports non-covalent association of two subunits, a trimerization domain, which supports non-covalent association of three subunits, a tetramerization domain or an even higher multimerization domain. Preferably, the multimerization domain is a dimerization domain, a trimerization domain, or a tetramerization domain.

Multimerization domains may be selected from prokaryotic or eukaryotic chaperones, preferably from ATP-independent chaperones. Specific examples of multimerization domains are the proteins FkpA, Skp, and SecB from *E. coli* or orthologs thereof from other prokaryotic organisms. FkpA is an ATP-independent periplasmic dimerization chaperone from *E. coli*. Skp is an ATP-independent periplasmic trimerization chaperone from *E. coli*. SecB is an ATP-independent cytosolic tetramerization chaperone from *E. coli*. Further suitable multimerization domains are heat shock proteins from eukaryotic or prokaryotic organisms, e.g., Hsp25, an ATP-independent eukaryotic cytosolic/nuclear oligomeric chaperone. A further suitable multimerization domain is MIP (macrophage infectivity potentiator), an ATP-independent dimerization chaperone which is structurally related with FkpA. ATP-dependent chaperones like GroEL, an ATP-dependent cytosolic heptamerisation chaperone from *E. coli* or ClpB, an ATP-dependent hexamerization chaperone from *E. coli* or ClpX are also suitable. Further, the multimerization domains may be selected from fragments or variants of the above polypeptides, which retain their ability of multimer formation.

The fusion polypeptide of the invention comprises a plurality of copies of an epitope segment. An epitope segment comprises an amino acid sequence recognized by an antibody. Thus, the polypeptide comprises multiple binding sites for an antibody which recognizes the respective epitope. Preferably, the amino acid sequence of the individual epitope segments is identical or substantially identical. It is, however, possible that one or more of the epitope segments are different as long as these differences do not negatively affect recognition by the antibodies to be detected. The fusion polypeptide comprises at least 2, preferably 2-10, more preferably 2-6 and most preferably 2, 3, 4, 5, or 6 copies of the epitope segments.

A multimer consisting of a plurality of individual fusion polypeptide subunits preferably comprises at least 4, more preferably at least 6 and most preferably at least 8 copies of an epitope segment. The multimer may comprise, e.g., up to 40, preferably up to 30 and most preferably up to 25 copies of an epitope segment.

Usually the fusion polypeptide comprises a plurality of copies of only a single epitope segment. In this case, the fusion polypeptide has a single antibody specificity. In some embodiments it is, however, envisaged that the fusion polypeptide comprises a plurality of copies of two or more different epitope segments, preferably of two different epitope segments. In this case, the fusion polypeptide is suitable for the detection of several types of antibody specificities.

The length of an epitope segment is usually at least 5 amino acids, preferably at least 6 amino acids and more preferably at least 8 amino acids. The maximum length of the epitope segment is usually 100-120 amino acids, preferably 80 amino acids, and more preferably 70 amino acids. Most preferably, the epitope segment has a length of 15-50 amino acids.

The individual epitope segments in the fusion polypeptide may be separated by spacer sequences. The spacer sequences are preferably sequences which are heterologous to the pathogenic organism from which the epitope segment is derived. For practical purposes, the spacer sequences are selected from sequences which barely if at all interfere with the use of the fusion polypeptide as test antigen for determining antibodies. This means that the spacer sequences are non-immunologically reactive against the antibodies to be tested. Preferably, the spacer sequences comprise glycine and/or serine residues. Especially preferred are polyglycine spacer sequences. The length of the spacer sequences is preferably from 1-10 amino acids, more preferably from 2-5 amino acids, and most preferably 3 or 4 amino acids. Especially preferred is a (Gly)3 spacer sequence.

Further, a spacer sequence may be present between a multimerization domain and the epitope segments. This spacer sequence may have a length of, e.g., 1-100 amino acids. Preferably, this spacer sequence is heterologous to the multimerization domain and the epitope segment. Preferably, the spacer sequence is as described above.

The epitope segments of the fusion polypeptide are antigen sequences from a pathogen which are capable of binding to antibodies raised in the course of an immunoreaction by an organism infected by the pathogen. The epitope sequences are preferably selected in order to be recognized by antibodies occurring in specific stages of infection, e.g., "early" epitopes, which are preferentially recognized by antibodies during an early infection state or "late" epitopes, which are preferentially recognized in a later state of infection. In a preferred embodiment, the epitope segment comprises an epitope which is specifically recognized by antibodies occurring in an early and/or acute phase of an infection with said pathogen. In an especially preferred embodiment, the epitope segment comprises an epitope which is specifically recognized by antibodies occurring in an early and/or acute phase of a primary infection with said pathogen. In still a further embodiment, the epitope segment comprises an epitope which is specifically recognized by antibodies occurring in a late phase of an infection with said pathogen or past infection. In yet another embodiment, the epitope segment comprises an epitope which is specifically recognized by antibodies occurring in a persisting or recurrent infection with said pathogen.

The epitope segment may be derived from any viral, bacterial, or protozoic pathogen which is capable of causing a detectable immune reaction, i.e., a generation of antibodies, particularly IgM antibodies as a result of an infection. For example, the pathogen is selected from the group consisting of

- herpes viruses such as human herpes simiplex virus 1 and 2 (HHV1 and HHV2), varicella zoster virus (HHV3), Epstein-Barr virus (HHV4/EBV), or human cytomegalovirus (HHV5) and human herpes viruses 6, 7, and 8, rubella virus,
- hepatitis viruses such as hepatitis A virus (HAV), hepatitis B virus (HBV), and hepatitis C virus (HCV),
- paramyxoviruses such as measles virus and mumps virus,
- a *Toxoplasma* organism, and
- a *Borrelia* organism.

Examples of suitable epitopes from these pathogens have been described in numerous documents as described in detail below. These documents and the references cited therein are herein incorporated by reference.

Specific detection of IgM molecules indicative of an early infection is clinically important for many viral, bacterial, and protozoic infections in man. The family of herpesviridae, e.g., comprises herpes simplex virus 1 and 2 (HHV1, HHV2), varicella zoster virus (HHV3), Epstein-Barr virus (HHV4), human cytomegalovirus (HHV5), and the human herpesviruses 6, 7, and 8. Human cytomegalovirus (HHV5) plays a key role in pregnancy routine diagnostics; it may cause devastating damage to the fetus when a child-bearing woman without humoral or cellular immunity against the virus undergoes primary infection during the first trimester of gestation.

By means of epitope mapping, a plurality of crucial immunological determinants has been identified in distinct herpes antigens. For instance, antibody reactivities of individual epitopes in the HCMV antigens pp150, p52, gB, and pp28 are summarized by Greijer et al., J. Clin. Microbiol. (1999) 37(1), 179-188. Further epitopes are described by Schoppel et al., J. Infect. Dis. (1997) 175 (3), 533-544. As far as herpes simplex virus is concerned, immunodominant epitopes have been mapped in the sequence 552-578 of mature glycoprotein G from HSV-2 (Marsden et al., J. Med. Virol. (1998) 56, 79-84; Liljeqvist et al., J. Gen. Virol. (1998) 79, 1215-1224) and to the sequence 112-127 of glycoprotein G1 from HSV-1 (Tunbäck et al., J. Gen. Virol. (2000) 81, 1033-1040), respectively. These epitopes may be incorporated into the fusion polypeptides of the invention.

Playing prominent roles as parameters in pregnancy screening, *Toxoplasma gondii* and rubella virus together with human cytomegalovirus and herpes simplex viruses type 1 and 2 constitute the TORCH family. Primary infections of pregnant women (lacking both humoral and cellular immunity) with these pathogens in the first trimester of gestation may lead to severe damage of the fetus. This necessitates a reliable differential diagnosis, which discriminates between primary and recurrent infections. As mentioned above, immunodominant determinants within several HCMV antigens are well known from literature, e.g., the sequences 595-636 and 1011-1048 from pp150, the sequences 266-293 and 295-312 from p52, the sequences 792-809 and 60-81 from glycoprotein B, and the sequences 1545 and 130-160 from pp28 (Greijer et al., supra). Similarly, major epitopes have been identified on the immunodominant envelope protein E1 from rubella virus. For instance, the region between amino acids 243-286 contains three neutralizing epitopes, as reported by Terry et al. (Terry et al., Arch. Virol. (1988) 98, 189-197). Another neutralizing E1 epitope has been characterized in the region between amino acids 213-239 (Mitchell et al., J. Clin. Microbiol. (1992) 30 (7), 1841-1847). At least one immunodominant epitope with neutralizing capacity has been identified on a second rubella envelope protein E2 (Green & Dorsett, J. Virol (1986) 57 (3), 893-898). An immunodominant T-cell epitope and several linear B-Cell epitopes have been localized in the E2 region 31-105 (McCarthy et al., J. Virol. (1993) 67 (2), 673-681; Wolinsky et al., J. Virol. (1991) 65, 3986-3994) These epitopes may be incorporated into the fusion polypeptides of the invention.

Several proteins from *Toxoplasma gondii* have been identified as immunodominant antigens: the dense granule proteins GRA1 (p24), GRA2 (p28), GRA4 (p41), GRA6 (p32), GRA7 (p29), and GRA8 (p35), the surface antigens SAG1 (p30) and SAG2 (p22), the rhoptry antigens ROP2 (p66) and ROP2 (p54), the matrix protein MAGI (p65), and the microneme proteins MIC3 and MIC5 (Pfrepper et al., Clin Diagn. Lab. Immunol. (2005) 12 (8), 977-982). For the detection of anti-*toxoplasma* IgM antibodies, a combination of GRA7, GRA8, and ROP1 has been suggested previously (Aubert et al., J. Clin. Microbiol. (2000) 38: 1144-1150). These epitopes may be incorporated into the fusion polypeptides of the invention.

Another important field in serology covers hepatitis viruses such as HAV, HBV, and HCV. Immunodominant antigens and the respective immunodominant epitopes are well known for each of these pathogens. For instance, the HBV nucleocapsid protein is the major target of the host immune response in chronic hepatitis B, and several immunodominant epitopes have been characterized. Important B-cell epitopes on the hepatitis B surface antigen (HBsAg) have been localized to amino acids 74-89, 130-138 (Salfeld et al., J. Virol. (1989) 63, 798-808), and 107-118 (Colucci et al., J. Immunol. (1988) 141, 4376-4380). These epitopes may be incorporated into the fusion polypeptides of the invention.

Immunodominant epitopes have been characterized for a plurality of hepatitis C antigens (summarized in Carlos et al., Clin. Immunol. (2004) 111, 22-27). For instance, epitopes of the immunodominant regions of Core (7-18), E2 (484-499), NS3 (1248-1265), and NS4 (1767-1786) have been defined as well as epitopes from the hypervariable regions of E2 HVR1 genotype 1a (386406), E2 HVR2 genotype 1a (472-485), E2 HVR1 genotype 1b (386406), and E2 HVR2 genotype 1b (472-485). These and other HCV epitopes may be incorporated into the fusion polypeptides of the invention and should prove useful for the development of a differential IgM immunoassay according to the present invention.

Other important human pathogens are the measles virus and the mumps virus, both of which belong to the family of paramyxoviridae, and each consist of six structural proteins. The nucleocapsid protein N of the measles virus is the main target of the humoral immune response, and the B-cell response against N is pivotal in the control of measles infection. Recently, the immunodominant epitopes were mapped within the C-terminus of the N antigen between amino acids 419 and 525. In particular, a linear epitope could be localized within a sequence of 440-448 (Zvirbliene et al., Arch. Virol. (2007) 152, 25-39). Similarly, the nucleocapside associated protein NP from mumps virus constitutes the main antigen determinant, and recombinant variants of NP exhibit high antigenicity and are well suited for the specific detection of IgM in mumps serology (Samuel et al., J. Med. Virol. (2002) 66, 123-130).

Immunodiagnostics of *Borrelia* (*B. burgdorferi, B. garinii, B. afzelii*) sparks growing interest due to the relentless spread of this spirochete. Due to forthcoming mild winters in the wake of the conspicuous climate change, it is presumed that the impact of *Borrelia* will even more increase in the near future. An immunodominant conserved region of the *Borrelia burgdorferi* VlsE antigen has been described which is well suited for sensitive and specific serodiagnosis (Liang et al., J.

Clin. Microbiol. (1999) 37 (12), 3990-3996). The so-called IR6 or C6 region (Liang & Philipp, Infect. Immun. (1999) 67, 6702-6706; Liang et al., J. Immunol. (999) 163(10) 5566-5573) comprises an invariable 26 amino acid segment which may be incorporated into the fusion polypeptides of the invention.

The fusion polypeptide is preferably used as a test reagent in a method for detecting an antibody, particularly an IgM antibody in a sample. For this purpose, the fusion protein may carry reporter and/or coupling groups. Examples of suitable reporter groups are groups detectable by optical means, e.g., fluorescent groups, luminescent groups, e.g., chemiluminescent groups, or particulate groups such as metal, e.g., gold or latex particles. Of course, further reporter groups such as enzymatic groups, radioactive groups, hapten groups, etc. are also suitable. Especially preferred are electrochemiluminescence reporter groups, particularly ruthenium groups such as ruthenium (bipyridine)3 or ruthenium (phenanthroline)3 groups. Especially preferred are also hapten reporter groups such as digoxigenin groups which may be detected with an anti-hapten antibody such as an anti-digoxigenin antibody.

In a further embodiment, the fusion polypeptide may carry at least one coupling group. A coupling group is a group for coupling the fusion polypeptide to a further compound or substance, e.g., a solid phase or a reporter group as defined above. The coupling group may be a group for covalent coupling or for non-covalent coupling. Preferably, the coupling group is a first partner of a specific binding pair which specifically interacts with the second partner of the binding pair. Preferred binding pairs are biotin/avidin, biotin/streptavidin, biotin/antibiotin antibody, hapten/anti-hapten antibody, and carbohydrate/lectin. Preferably, the coupling group is a biotin group including biotin derivatives, i.e., compounds structurally related to biotin which retain the ability of binding to streptavidin and/or avidin.

The fusion polypeptide may be bound to reporter and/or coupling groups according to conventional means. For example, conjugation reagents comprising reporter and/or coupling groups may be prepared. These reagents may further comprise a group which can react with groups present on the polypeptide, e.g., hydroxy, amino, carboxy, and/or thio groups. Specific examples of coupling groups are active ester groups, e.g., N-hydroxysuccinimide groups or maleimide groups.

The invention further refers to a nucleic acid molecule encoding a fusion polypeptide as described above. The nucleic acid molecule is preferably a DNA molecule. In order to increase the stability of the nucleic acid molecule, it is preferred that the portions thereof encoding the individual epitope segments (which are preferably identical at the amino acid level) have a different nucleotide sequence within the scope of degeneracy of the genetic code wherein different nucleotide triplet codons encoding the same amino acids are used. More preferably, each portion encoding an individual identical epitope segment has a nucleotide sequence which is different from the other portions.

Further, the invention refers to an expression vector comprising at least one nucleic acid molecule as described above operatively linked to an expression control sequence. The expression vector may be a prokaryotic or eukaryotic vector further comprising genetic elements for maintenance and propagation in the respective host cell such as origin of replication and/or selection marker genes. The expression control sequence may be a prokaryotic or eukaryotic expression control sequence which is constitutive or inducible. The expression control sequence is chosen to allow efficient expression in a desired host cell. Examples of suitable expression vectors and expression control sequences are known to the skilled person and described in standard textbooks such as Sambrook et al., Molecular Cloning—A Laboratory Manual (1989), Cold Spring Harbour Press, or are commercially available.

Further, the invention refers to a host cell transfected or transformed with a nucleic acid molecule or an expression vector as described above. The host cell may be a prokaryotic cell, e.g., a gram-negative bacterial cell such as *E. coli*, or a eukaryotic cell, e.g., a yeast cell, an insect cell, or a mammalian cell. The host cell may be used for the recombinant preparation of a fusion polypeptide as described above. Preferably, the recombinant production comprises the steps of providing a host cell as described above, cultivating said host cell under conditions wherein the fusion polypeptide is expressed, and isolating said fusion polypeptide.

As indicated above, the fusion polypeptide of the present invention is preferably used as a detection reagent in a method for detecting an antibody in a sample. The antibody is preferably an IgM antibody. More preferably, the detection comprises a differential determination of IgM antibodies. In an especially preferred embodiment, the antibody is an IgM antibody occurring in an early or acute phase of an infection, particularly of a primary infection with a pathogen.

In a further embodiment, the fusion polypeptide may be used as an interference elimination reagent in a method for detecting an antibody in a sample. In this embodiment, the antibody is preferably an IgG antibody.

The invention also refers to a test reagent kit for detecting an antibody in a sample comprising at least one fusion polypeptide and further test components. The test reagent may comprise a single fusion polypeptide comprising a single type of epitope or a single fusion polypeptide comprising two or more different types of epitopes or two or more fusion polypeptides comprising a single type of epitope or two or more different types of epitopes. The fusion polypeptide of the invention may be a detection reagent or an interference elimination reagent. If the fusion polypeptide is a detection reagent, it preferably comprises reporter and/or coupling groups as described above. If the fusion polypeptide is an interference elimination reagent, it preferably does not comprise any reporter group. The interference elimination reagent is characterized in that its effective epitope concentration or density differs from the effective epitope concentration of the detection reagent. Preferably, the epitope concentration or epitope density of the interference elimination reagent is lower than that of the detection reagent.

The present invention also refers to a method for detecting an antibody directed against a pathogenic organism in a sample comprising the steps of incubating said sample with a test reagent comprising at least one fusion polypeptide as described above and further test components and determining the presence and/or concentration of said antibody in said sample by evaluating the reaction of sample components with the test reagent.

The test reagent preferably comprises a detection reagent and at least one interference elimination reagent, and the determination step comprises determining the reaction of desired sample components, i.e., the type of antibody to be detected, with the detection reagent, wherein undesired sample components, e.g., antibodies of a different class such as IgG and/or IgM antibodies characteristic for non-relevant infection stages, are captured by the at least one interference elimination reagent. In a preferred embodiment, the antibody to be detected is an IgM antibody, more preferably an IgM antibody occurring in an early and/or acute phase of an infection, particularly of a primary infection. In this case, the test reagent preferably further comprises an interference elimination reagent, for capturing IgG antibodies, and/or an interference elimination reagent for capturing IgM antibodies occurring in a late phase of an infection and/or in a recurrent infection, wherein the interference elimination reagent does not carry a reporter group. The interference elimination reagent is characterized in that its effective epitope concentration or density differs from the effective epitope concentration or density of the detection reagent. In case the detection reagent is provided for differentially detecting an IgM antibody occurring in an early and/or acute phase of an infection, the effective epitope concentration or density of the interference elimination reagent is lower. For example, the epitope concentration or density of the interference elimination reagent should not exceed fifty percent of the epitope density of the detection reagent.

Preferably, the sample is preincubated with the interference elimination reagent(s) before it is contacted with the detection reagent.

Examples of IgG interference elimination reagents are antigens comprising monomeric epitope comprising fragments. In a preferred embodiment, the IgG interference elimination reagents are fusion polypeptides comprising a monomeric chaperone domain such as SlyD from E. coli and a single copy of an epitope comprising fragment from the pathogen. The epitope present in the IgG interference elimination reagent may be the same as in the detection reagent.

Examples of interference elimination reagents for capturing and thus quenching late IgM antibodies are multimeric antigens comprising a plurality of epitopes. In this embodiment, the interference elimination reagent, however, comprises a lower number of epitopes than the detection reagent. Preferably, the interference elimination reagent comprises at least two epitopes and up to half the number of epitopes of the respective detection reagent. Surprisingly, it was found that such a multimeric interference elimination reagent is capable of capturing and thus quenching late IgM antibodies, which were found to have a higher affinity to the epitope than the early antibodies to be detected without having a significant negative effect on the detection of the desired early IgM antibodies. Thus, for example, the IgM interference elimination reagent may comprise 2-6, e.g., 2, 3, 4, or 6 copies of the epitope, whereas an early IgM detection reagent may comprise at least 8, e.g., at least 12 or 16 copies of the epitope comprising fragment. The interference elimination agent may, e.g., be a fusion polypeptide comprising a monomeric chaperone domain such as SlyD and a plurality of epitopes or a fusion polypeptide comprising a multimerization domain and a single epitope or 2 copies of the epitope. The epitope present in the IgM interference elimination reagent may preferably be the same as in the detection reagent.

The method of the invention is preferably carried out as a double antigen sandwich test wherein the test reagent comprises two fusion polypeptides as described above wherein the first fusion polypeptide carries a reporter group or carries a coupling group which can be bound to a reporter group. The second fusion polypeptide is bound to a solid phase or carries a coupling group for immobilization to a solid phase. In this embodiment, the antibody analyte is determined by forming a complex with the first and second fusion polypeptide and detecting said complex on said solid phase.

In a further preferred embodiment, the method of the invention may be carried out as an indirect test wherein the test reagent comprises one fusion polypeptide which carries a coupling group for immobilization to a solid phase and a receptor recognizing the antibody class to be determined, e.g., an anti-human IgM antibody wherein the receptor carries a reporter group and wherein the antibody is determined by forming a complex with the fusion polypeptide and the receptor on a solid phase. Alternatively, the indirect test may comprise the use of an immobilized or immobilizable receptor and a fusion polypeptide comprising a reporter group.

As explained above, the present invention allows differential diagnosis of IgM antibodies. Thus, a further embodiment refers to a specific determination of IgM antibodies occurring in a late phase of an infection and/or in a recurrent infection. In this embodiment, the detection reagent comprises at least one multimeric antigen having low epitope density as described above, e.g., preferably a fusion polypeptide comprising 2-6, e.g., 2, 3, 4, or 6 copies of the epitope, which might be suitable as an interference elimination reagent in a test for "early" IgM antibodies, but which carries reporter and/or coupling group. Further, the test preferably comprises an interference elimination reagent for capturing IgG antibodies as described above and/or an interference elimination reagent for capturing IgM antibodies occurring in an early phase of an infection, particularly in an early phase of a primary and/or acute infection. Preferably, the interference, elimination reagent for "early" IgM antibodies corresponds to the test reagent for determining "early" IgM antibodies but without reporter groups. Alternatively, a differential IgM determination may be carried out by differential analysis, i.e., a first test in the presence of a test reagent for detecting only a single type of IgM antibodies (e.g., "early" antibodies) and a second test with a test reagent for detecting all IgM antibodies.

In still a further embodiment, the antibody to be detected is an IgG antibody. In this case, the detection reagent is a monomeric antigen, e.g., a monomeric fusion protein as described above. Further, the test reagent comprises an interference elimination reagent for capturing IgM antibodies which is a multimeric antigen comprised of a complex of a fusion polypeptides of the present invention as described above wherein each fusion polypeptide comprises a multimerization domain and a plurality of a copies of an epitope. The interference elimination reagent preferably does not contain a reporter group.

A further aspect of the invention refers to a method for differentially detecting an IgM antibody in a sample wherein the sample may comprise an interfering antibody selected from an interfering IgM antibody and/or an interfering IgG antibody. According to this method, a test reagent is used which comprises a multiple antigen, i.e., an antigen comprising a plurality of epitope copies to which the antibody to be detected can bind. Preferably the test antigen comprises a reporter group.

The inventive method is based on the use of a multimeric test antigen with a preselected effective epitope density and/or concentration which is adapted to the type of IgM antibody to be detected. The test antigen is preferably combined with an interference elimination reagent adapted to eliminate binding of undesired IgM antibody types to the test antigen.

The effective epitope density or concentration of the test antigen is adapted for the type of IgM antibody to be detected, e.g., an IgM antibody occurring in an early or acute phase of an infection, preferably of a primary infection or alternatively an IgM antibody occurring in a late phase of an infection, an IgM antibody occurring past infection, and/or an IgM antibody occurring in a persisting or recurring infection. Preferably, the differential IgM antibody detection is carried out in the presence of at least one interference elimination reagent which may comprise an antigen which binds specifically to an interfering IgM antibody and/or an antigen which binds specifically to an interfering IgG antibody.

In a preferred embodiment, the method comprises the steps of:
- incubating said sample with a test reagent comprising:
  - at least one receptor R1 which binds specifically to IgM antibodies,
  - at least one receptor R2 which binds specifically to the IgM antibody to be detected differentially, wherein R2 carries a reporter group,
  - optionally at least one receptor R3 which binds specifically to the interfering IgM antibody, and
  - optionally a receptor R4 which binds specifically to an IgG antibody,
- allowing the following complexes to form:
  - a complex comprising R1, said IgM antibody to be detected differentially, and R2, said complex carrying a reporter group,
  - optionally a complex comprising R3 and said interfering IgM antibody, thereby eliminating interfering binding of said interfering IgM antibody to R2, and
  - optionally a complex comprising R4 and said interfering IgG antibody thereby eliminating interfering binding of said interfering IgG antibody to R2, and
- determining said reporter group bound by R2 to said IgM antibody to be detected differentially as a measure of said IgM antibody in said sample.

The test may be carried out in a double antigen sandwich assay format or an indirect format as described above. In a double antigen sandwich format, the receptor R1 may be a multimeric antigen which specifically binds to the IgM; antibody to be detected. In an indirect test format, the receptor R1 may be a receptor which specifically binds to any IgM, particularly any human IgM in the sample, e.g., an anti-human IgM antibody. The binding of the desired IgM antibody type is preferably detected on a solid phase. For this purpose, the receptor R1 preferably carries a coupling group for immobilization to a solid phase, e.g., a coupling group as described above, preferably biotin. The reporter group of the labelled receptor R2 is a reporter group as described above, preferably an electrochemiluminescence group. When using interference elimination reagents, i.e., the receptors R3 and/or R4, they are preferably preincubated with the sample before the receptors R1 and/or R2 are added.

The IgG interference elimination receptor R4 is preferably a monomeric receptor, i.e., an antigen which comprises a single epitope copy. The test receptor R2 and the IgM interference elimination receptor R3 are multimeric receptors, i.e., antigens comprising multiple epitope copies. R2 and R3, however, have different effective epitope densities or concentrations and thus bind preferentially to different types of IgM antibodies. For the differential determination of IgM antibodies occurring in an early or acute phase of an infection, preferably of a primary infection, the labelled receptor R2 may comprise, e.g., at least 6, preferably at least 8, and more preferably at least 12 epitope copies, up to 40, preferably up to 30, and most preferably up to 25 epitope copies recognized by the IgM antibody to be detected. The interference elimination receptor R3, which is specific for "late" IgM antibodies, has an effective epitope density or concentration, which may be, e.g., at least two times as low, preferably at least three times as low, and most preferably at least 4 times as low or even lower compared to the epitope density or concentration of the test receptor R2. In this embodiment, the interference elimination receptor R3 may comprise 2-8, preferably 3-6, epitope copies.

The multimeric test receptor R2 is preferably a fusion polypeptide as described above for the first aspect of the invention. The multimeric interference elimination receptor R3 may also be a fusion polypeptide as described above. It should be noted, however, that in this embodiment of the invention, also conventional multimeric test antigens may be used, e.g., multimeric antigens obtained by chemical crosslinking of monomeric antigens or epitopes by homo- or hetero-bifunctional crosslinkers. Alternatively, the multimeric antigens may be carrier molecules, e.g., carrier polypeptides with peptide epitope sequences coupled thereto or multimeric peptides, e.g., branched multimeric peptides as described in Lee et al. (Nature Biotechnology 23 (2005), 1517-1526), the content of which is herein incorporated by reference.

Still a further aspect of the invention refers to a test reagent for differentially detecting an IgM antibody directed against a pathogen in a sample wherein the sample may comprise an interfering antibody selected from an interfering IgM antibody and/or an interfering IgG antibody comprising:
- at least one receptor R1 which binds specifically to IgM antibodies,
- at least one receptor R2 which binds specifically to the IgM antibody to be detected differentially, wherein R2 carries a reporter group,
- optionally at least one receptor R3 which binds specifically to the interfering IgM antibody, and
- optionally a receptor R4 which binds specifically to an IgG antibody.

The present invention is further explained by the figures and examples.

SPECIFIC EMBODIMENTS

Example 1

Manufacture of Fusion Polypeptide Test Reagents

1. Materials and Methods 1.1. Materials and Reagents

Guanidinum-Cl (GdmCl) was purchased from NIGU (Waldkraiburg, Germany). Complete EDTA-free protease inhibitor tablets, imidazole and EDTA were from Roche Diagnostics GmbH (Mannheim, Germany), all other chemicals were analytical grade from Merck (Darmstadt, Germany). Ultrafiltration membranes (YM10, YM30) were purchased from Amicon (Danvers, Mass., USA), microdialysis membranes (VS/0.025 µm) and ultrafiltration units (biomax ultrafree filter devices) were from Millipore (Bedford, Mass., USA). Cellulose nitrate and cellulose acetate membranes (1.2 µm/0.45 µm/0.2 µm) for the filtration of crude lysates were from Sartorius (Göttingen, Germany).

1.2 Cloning of Expression Cassettes

The sequences of Skp, FkpA and SlyD were retrieved from the SwissProt (UniProt) database (SkP: SwissProt Accession No. P11457; FkpA: SwissProt Accession No. P45523; SlyD: SwissProt Accession No. P0A9K9). The genes for *E. coli* Skp, FkpA and SlyD were amplified by PCR from *E. coli* strain BL21 (DE3), restricted and ligated into the pET24a expression vector (Novagen, Madison, Wis., USA). In order to circumvent covalent adduct formation via disulfide bridges, the cysteine-rich C-terminal part of SlyD (166-196) was removed, and the truncated SlyD version AA 1-165 (SEQ ID NO: 1) was used as a fusion partner. In order to ensure cytosolic expression of the target molecules, the signal sequences of the periplasmic chaperones FkpA and Skp were omitted. Thus, FkpA version AA 26-270 (SEQ ID NO: 2) and Skp version AA 21-161 (SEQ ID NO: 3) were used as modules in the fusion polypeptides. The expression cassettes for the fusion proteins were designed as described by Scholz et al. (J. Mol. Biol. 345 (2005), 1229-1241). QuikChange (Stratagene, La Jolla, USA) and standard PCR techniques were used to generate point mutations, deletion and insertion variants or restriction sites. All recombinant protein variants contained a C-terminal hexahistidine tag to facilitate Ni-NTA-assisted purification and refolding.

1.3 Expression, Purification and Refolding of Fusion Protein Variants

All polypeptide fusion variants were purified by using virtually identical protocols. E. coli BL21 (DE3) cells harboring the particular pET24a expression plasmid were grown at 37° C. in LB medium plus kanamycin (30 µg/ml) to an OD600 of 1.5, and cytosolic overexpression was induced by adding 1 mM isopropyl-β-D-thiogalactoside. Three hours after induction, cells were harvested by centrifugation (20 min at 5000 g), frozen and stored at −20° C. For cell lysis, the frozen pellet was resuspended in chilled 50 mM sodium phosphate pH 8.0, 7.0 M GdmCl, 5 mM imidazole and the suspension was stirred for 2 h on ice to complete cell lysis. After centrifugation and filtration (cellulose nitrate membrane, 0.45 µm/0.2 µm), the lysate was applied onto a Ni-NTA column equilibrated with the lysis buffer including 5.0 mM TCEP (tris(2-carboxyethyl)phosphine). The subsequent washing step was tailored for the respective target protein and ranged from 10-25 mM imidazole (SlyD and FkpA fusion proteins) to 30 mM imidazole (Skp fusion proteins) in 50 mM sodium phosphate pH 8.0, 7.0 M GdmCl, 5.0 nM TCEP. At least 10-15 volumes of the washing buffer were applied. Then, the GdmCl solution was replaced by 50 mM sodium phosphate pH 7.8, 100 mM NaCl, 10 mM imidazole, 5.0 mM TCEP to induce conformational refolding of the matrix-bound protein. In order to avoid reactivation of copurifying proteases, a protease inhibitor cocktail (Complete EDTA-free, Roche) was included in the refolding buffer. A total of 15-20 column volumes of refolding buffer were applied in an overnight reaction. Then, both TCEP and the Complete EDTA-free inhibitor cocktail were removed by washing with 3-5 column volumes 50 mM sodium phosphate pH 7.8, 100 mM NaCl, 40 mM imidazole. The native protein was then eluted by 250 mM imidazole in the same buffer. Protein-containing fractions were assessed for purity by Tricine-SDS-PAGE as described by Schägger and von Jagow (Anal. Biochem. 166 (1987), 368-379) and pooled. Finally, the proteins were subjected to size-exclusion-chromatography (SUPERDEX HiLoad, Amersham Pharmacia) and the protein-containing fractions were pooled and concentrated in an Amicon cell (YM10).

The following Skp fusion polypeptides were produced:

```
Skp-ppUL32-X1      (SEQ ID NO: 4)
and

Skp-ppUL32-X4      (SEQ ID NO: 5)
```

These fusion polypeptides comprise the Skp fusion module and one (X1) or four (X4) copies of the human cytomegalovirus (HMCV) epitope ppUL32. This epitope corresponds to amino acids 587-640 of HCMV large structural phosphoprotein pp150 (Uniprot ID P08318).

```
Skp-pp150-X1       (SEQ ID NO: 6)
and

Skp-pp 150-X4      (SEQ ID NO: 7)
```

These fusion polypeptides comprise the Skp fusion module and one (X1) or four (X4) copies of the HMCV pp150 epitope, which corresponds to amino acids 999-1048 of HCMV pp150.

```
Skp-p52-X1         (SEQ ID NO: 8)
and

Skp-p52-X4         (SEQ ID NO: 9)
```

These fusion polypeptides comprise the Skp fusion module and one (X1) or four (X4) copies of the HMCV p52 epitope corresponding to amino acids 254-293 of HCMV polymerase accessory protein p52 (Uniprot ID P16790).

1.4 Spectroscopic Measurements

Protein concentration measurements were performed with an Uvikon XL double-beam spectrophotometer. The molar extinction coefficients ($\epsilon 280$) were determined by using the procedure described by Pace et al., (Protein Sci. 4 (1995), 2411-2423).

1.5 Coupling of Ruthenium Moieties to the Fusion Proteins

The lysine ε-amino groups of the fusion proteins were modified at protein concentrations of ~10 mg/ml with N-hydroxy-succinimide activated ruthenium labels. The label:protein molar ratio varied from 2:1 to 7:1, depending on the respective fusion protein. The reaction buffer was 150 mM potassium phosphate (pH 8.0), 50 mM potassium chloride, 1 mM EDTA. The reaction was carried out at room temperature for 10 minutes and stopped by adding buffered L-lysine to a final concentration of 10 mM. To avoid hydrolytic inactivation of the labels, the respective stock solutions were prepared in dried. DMSO (seccosolv quality, Merck, Germany). DMSO concentrations up to 20% in the reaction buffer were well tolerated by all fusion proteins studied. After the coupling reaction, unreacted free label and the organic solvent were removed by passing the crude protein conjugate over a gel filtration column (SUPERDEX 200 HiLoad).

1.6 Immunological Reactivity of Chaperone Fusion Proteins

The chaperone fusion modules were used to detect IgM antibodies directed against the antigens p52 and pp150 from HMCV, which abundantly occur in human sera at the onset of an CMV infection. The immunological reactivity was challenged in an automated ELECSYS 2010 analyzer (Roche Diagnostics GmbH) using the µ-Capture format (i.e., the total IgM collective is captured and immobilized to the solid phase via a specific anti-IgM IgG.).

Signal detection in the ELECSYS immunoassay is based on electrochemiluminescence. The biotin-conjugated IgM capture antibody is immobilized on the surface of streptavidin-coated magnetic beads, whereas the signaling antigen bears a complexed ruthenium cation as the luminescent moiety. In the presence of anti-p52/anti-pp150 IgM antibodies, the chromogenic ruthenium complex is bridged to the solid phase and emits light at 620 nm after excitation at a platinum electrode. The signal output is in arbitrary light units. For their use as ELECSYS antigens, the soluble p52/pp150 fusion proteins under study were concentrated and modified with N-hydroxy-succinimide activated ruthenium moieties as described by Scholz et al. (2005), supra. The concentration of the chaperone fusion variants in the immunoassay measurements was ~20-100 ng/ml. At least five negative sera were used as controls. In order to minimize false positive results, chemically polymerized unlabeled chaperone modules were added to the samples as an anti-interference substance.

2. Results

2.1 High Expression Yield

Skp, FkpA, SlyD and their fusion variants were abundantly overexpressed in the BL21 (DE3) *E. coli* strains. Due to the high rate of synthesis, the target proteins partially accumulated as inclusion bodies in the *E. coli* cytosol. Matrix-coupled refolding turned out to be the method of choice to renature Skp, FkpA, SlyD and their fusion variants at very high yields. Essentially, the renaturing protocol followed the method developed for SlyD fusion proteins (Scholz et al. (2005), supra.; Scholz et al., Biochemistry 45 (2006), 20-33). Following the coupled purification and refolding protocol, more than 20 mg of target protein could be obtained from 1 g of *E. coli* wet cells. As an example, the purification of Skp-p52-X4 as documented by SDS-PAGE is shown in FIG. 1.

Example 2

CMV IgM Test

A test for determining IgM antibodies directed against CMV was developed. This test allows differentiation between an acute/early primary infection stage and a late infection stage or a recurrent infection. The detection reagent comprises complexes each comprising a three units of a fusion polypeptide each comprising the trimerization domain Skp and 4 CMV epitopes (either UL32 or 150) labelled with ruthenium (bipyridine)3 (BPRu). Thus, a multimeric molecule of the detection reagent comprises 12 epitope copies. The test is carried out in the absence or presence of interference elimination reagents, i.e., the monomeric IgG interference elimination reagent SlyD-X, wherein X is the UL32 or 150 epitope, the dimeric or tetrameric IgM interference elimination reagents (FkpA-X)$_2$ and (FkpA-X2)$_2$, wherein FkpA is a dimerization domain and X is the epitope UL32 or pp150, and the trimeric or hexameric IgM interference elimination reagents (Skp-X)3 and (Skp-X2)3 wherein Skp is a trimerization domain and X the UL32 or pp150 epitope.

1. Materials and Methods

1.1 Components

Buffer B1
Variant 1:
  50 mM MES buffer pH 6.5, 150 mM NaCl; 1 mM EDTA, 0.1% methylisothiazolone and oxypyrione, prolidocanol and 0.2% bovine serum albumin (BSA)
  1 mg/L biotinylated monoclonal Mab-anti human IgM.
Variant 2:
  Like variant 1 plus 2 mg/L SlyD-pp(UL32)×1 and 2 mg/ml SlyD-pp(150)×1
Variant 3:
  Like variant 1 plus 2 mg/L FkpA-pp(UL32)×1 and 2 mg/ml FkpA-pp(150)×1
Variant 4:
  Like variant 1 plus 2 mg/L Skp-pp(UL32)×1 and 2 mg/ml Skp-pp(150)×1
Buffer B2
  50 nM MES buffer pH 6.5, 150 mM NaCl; 1 mM EDTA, 0.1% methylisothiazolone and oxypyrione, prolidocanol and 0.2% bovine serum albumin (BSA).
Immunological Components in B2: Ruthenylated CMV Antigens.
  40 ng/ml Skp-(pp150)×4-BPRu and 40 ng/ml Skp-(UL32)×4-BPRu

2. Test Procedure on ELECSYS 2010 Instrument

10 µl diluted serum samples (1:20 with ELECSYS Diluent Universal)+75 µl buffer B1. After an incubation time of 9 minutes 75 µl buffer B2 and 40 µl streptavidin coated beads are added. After 9 minutes the mixture is transported to the measuring cell and the ECL signal is measured.

3. Results

The test results are shown in Tables 1 and 2.

TABLE 1

| Status of Infection | Variant 1 without inhibition | Variant 2 with SlyD-X inhibition (monomer) | | Variant 3 with FkpA-X inhibition (dimer and tetramer) | | Variant 4 with Skp-X inhibition (trimer and hexamer) | | Avidity Assay RADIM |
|---|---|---|---|---|---|---|---|---|
| | counts | counts | % (to Var. 1) | counts | % (to Var. 1) | counts | % (to Var. 1) | % Avidity |
| non infected | 724 | 759 | 104.8% | 750 | 103.6% | 757 | 104.6% | |
| non infected | 663 | 650 | 98.0% | 663 | 100.0% | 660 | 99.5% | |
| non infected | 607 | 604 | 99.5% | 601 | 99.0% | 617 | 101.6% | |
| non infected | 632 | 641 | 101.4% | 629 | 99.5% | 649 | 102.7% | |
| non infected | 795 | 804 | 101.1% | 787 | 99.0% | 777 | 97.7% | |
| acute | 4494 | 4401 | 97.9% | 4365 | 97.1% | 3653 | 81.3% | 12% |
| acute | 6713 | 6439 | 95.9% | 6165 | 91.8% | 5482 | 81.7% | 14% |
| acute | 12713 | 11905 | 93.6% | 11438 | 90.0% | 10081 | 79.3% | 22% |
| acute | 25583 | 24779 | 96.9% | 23140 | 90.5% | 20089 | 78.5% | 22% |
| acute | 101418 | 105922 | 104.4% | 103361 | 101.9% | 92796 | 91.5% | 11% |
| acute | 10651 | 10442 | 98.0% | 10060 | 94.5% | 8480 | 79.6% | 9% |
| acute | 16468 | 16148 | 98.1% | 15054 | 91.4% | 11905 | 72.3% | |
| acute | 104219 | 110150 | 105.7% | 110754 | 106.3% | 107816 | 103.5% | |
| acute | 219105 | 215878 | 98.5% | 202350 | 92.4% | 171314 | 78.2% | |
| past infection | 3610 | 3255 | 90.2% | 1545 | 42.8% | 1280 | 35.5% | 87% |
| past infection | 10995 | 7779 | 70.8% | 3717 | 33.8% | 3183 | 28.9% | 92% |
| reactivation | 12388 | 10145 | 81.9% | 4173 | 33.7% | 2651 | 21.4% | |
| reactivation | 6542 | 5579 | 85.3% | 2493 | 38.1% | 1791 | 27.4% | |
| reactivation | 8649 | 8025 | 92.8% | 3116 | 36.0% | 1892 | 21.9% | |
| reactivation | 9959 | 9548 | 95.9% | 5761 | 57.8% | 4976 | 50.0% | |

TABLE 2

| Status of Infection | Variant 1 without inhibition | Variant 2 with SlyD-X inhibition (monomer) | | Variant 3 with FkpA-X inhibition (dimer and tetramer) | | Variant 4 with Skp-X inhibition (trimer and hexamer) | | Avidity Assay RADIM |
|---|---|---|---|---|---|---|---|---|
| | counts | counts | % (to Var. 1) | counts | % (to Var. 1) | counts | % (to Var. 1) | % Avidity |
| non infected | 724 | 759 | 104.8% | 750 | 103.6% | 757 | 104.6% | |
| non infected | 663 | 650 | 98.0% | 663 | 100.0% | 660 | 99.5% | |
| non infected | 632 | 641 | 101.4% | 629 | 99.5% | 649 | 102.7% | |
| non infected | 795 | 804 | 101.1% | 787 | 99.0% | 777 | 97.7% | |
| acute | 18982 | 19145 | 100.9% | 18905 | 99.6% | 16878 | 88.9% | 18% |
| acute | 31865 | 31861 | 100.0% | 29462 | 92.5% | 24688 | 77.5% | 18% |
| acute | 32918 | 32801 | 99.6% | 30490 | 92.6% | 25012 | 76.0% | 11% |
| acute | 41662 | 41577 | 99.8% | 39666 | 95.2% | 34284 | 82.3% | 11% |
| acute | 25223 | 25171 | 99.8% | 23405 | 92.8% | 19732 | 78.2% | 13% |
| acute | 52253 | 52175 | 99.9% | 48414 | 92.7% | 40789 | 78.1% | 15% |
| acute | 20874 | 20687 | 99.1% | 19276 | 92.3% | 16271 | 77.9% | 7% |
| acute | 16587 | 15791 | 95.2% | 16218 | 97.8% | 14982 | 90.3% | 11% |
| acute | 47801 | 48075 | 100.6% | 45351 | 94.9% | 41383 | 86.6% | 18% |
| past infection | 8432 | 8736 | 103.6% | 4966 | 58.9% | 2967 | 35.2% | 83% |
| past infection | 14439 | 11351 | 78.6% | 2508 | 17.4% | 1910 | 13.2% | 61% |
| past infection | 4693 | 3212 | 68.4% | 976 | 20.8% | 722 | 15.4% | 93% |
| past infection | 4803 | 4468 | 93.0% | 1710 | 35.6% | 1112 | 23.2% | 57% |
| past infection | 6058 | 5855 | 96.6% | 3789 | 62.5% | 2582 | 42.6% | 71% |
| past infection | 28152 | 27962 | 99.3% | 18064 | 64.2% | 12521 | 44.5% | 79% |

4. Analysis of Results

Sera from non infected individuals, from patients suffering acute infection and from patients with past infection were subjected to an immunological assay based on the μ-capture format as described. The results are summarized in Table 1. The first column (variant 1) illustrates the signals obtained in the absence of any interference elimination reagent or quenching module. The counts with the CMV-negative human sera range around 700, and there is a clear discrimination between negative and positive sera. The second column (variant, 2) displays the signals obtained in the presence of the monomeric quenching-module SlyD-X. As evidenced by the residual signal strength (in %), the quenching effect of SlyD-X is negligible both with acute sera und with sera from past infections. This is in line with the expectations, since SlyD-X, as a monomer, should not be able to interact efficiently with polyvalent IgM molecules.

The third column (variant 3) exhibits the signals obtained in the presence of the dimeric quenching module FkpA-X. The residual signal strength evidences a negligible quenching effect of FkpA-X with acute sera and a significant quenching effect of FkpA-X with past infection sera. This finding reflects the higher epitope (X) density of FkpA-X with respect to SlyD-X. Obviously, FkpA-X interacts significantly with mature IgM molecules from past CMV infections, but it interacts rather weakly with immature, early IgM molecules from acute CMV infections.

In the penultimate column (variant 4), the quenching effects of the trimeric interference elimination reagent Skp-X are highlighted. Some signal quenching is found in acute sera, but a much higher signal quenching is observed in past infection sera. This is indicative for an interaction of the quenching module Skp-X with both early and late IgM molecules. Since the interaction of Skp-X with late IgM molecules is much higher compared to that with early IgM molecules, a differential detection of early IgM antibodies indicative for an acute infection is possible.

In summary, SlyD-X, FkpA-X and Skp-X do interact with IgM molecules directed against the epitope X, thereby quenching the signal μ-capture assay, in which Skp-X4 is used as the signaling antigen. The relative quenching efficiency increases in the order SlyD-X<FkpA-X<Skp-X, corresponding to the effective epitope density. The quenching efficiency is high with mature IgM molecules (from past infections), and it is rather low with immature IgM molecules (from acute infections).

Our findings enable a clear discrimination between early and late infections, e.g., viral infections. By using a labeled detection reagent with high epitope density such as an Skp-X4 detection module (12 epitope copies) and unlabelled quenching modules with a lower epitope density of the SlyD-X (1 epitope copy), FkpA-X (2 epitope copies) or Skp-X (3 epitope copies) type, a discrimination between early and, late infections can be made, which is clinically important. Hitherto, this discrimination has not been possible between different IgM fractions but has been attempted by performing IgG avidity tests: in short, IgG is detected in the absence and in the presence of non-denaturing concentrations of a chaotropic agent such as, e.g., urea or guanidinium chloride. The chaotrope preferentially reduces the binding of immature ("early") IgG molecules, but it does only barely affect the binding properties of mature, high-affinity ("late") IgG molecules. The ratio of the signal height in the presence and the absence of chaotrope yields the fraction of high-affinity (chaotope-resistant) IgG molecules. A high percentage in an avidity test reflects a predominant fraction of high-affinity IgG molecules, and a low percentage reflects a predominant fraction of low-affinity (early) IgG molecules. Thus, high percentages in an avidity test are indicative of a late infection, whereas low percentages are indicative of an early infection.

The last column in Tables 1 and 2 summarizes the results of acute and past infection sera, which were subjected to a commercial IgG avidity assay (RADIM). It becomes evident that the acute sera exhibit low residual signals (<20%), whereas past infection sera exhibit high residual signals. (>60%). These results are in excellent agreement with the inventive quenching approach. This is remarkable, since the inventive approach focuses on the differential detection of IgM molecules, whereas avidity assays in general focus on the differential detection of IgG molecules. The information gained by the different approaches is complementary: imma ture immunoglobulins (concomitant with early immune responses) lead to a high quenching in an IgG avidity assay (last column), but to a rather low quenching in the inventive Skp-X inhibition assay (penultimate column).

Mature immunoglobulins (concomitant with past or recurrent infections) lead to a low quenching in an IgG avidity assay (last column), but to a fairly high quenching in the inventive Skp-X inhibition assay. Immature immunoglobulins (concomitant with acute or early infection) lead to a high quenching in an IgG avidity assay, but to a low quenching in the Skp-X inhibition assay according to the invention. Thus, the inventive approach on the differential detection of IgM molecules adds valuable information to the diagnostic field whenever it is important to differentiate between early and later stages of an infection and to detect early stages of an infection.

What is claimed is:

1. A fusion polypeptide comprising at least one multimerization domain and a plurality of copies of an epitope segment from a pathogenic organism, wherein the multimerization domain, which supports multimerization of individual polypeptide molecules, is Skp from *E. coli*, and wherein the epitope segment comprises an epitope which is specifically recognized by antibodies occurring in a specific phase of infection, and wherein the fusion polypeptide is capable of forming a multimer.

2. The fusion polypeptide of claim 1, wherein said plurality is 2-10 copies.

3. The fusion polypeptide of claim 1, wherein the epitope segment has a length of from 5-120 amino acids.

4. The fusion polypeptide of claim 1, wherein the epitope segment has a length of from 15-50 amino acids.

5. The fusion polypeptide of claim 1, wherein a spacer sequence separates two epitope segments.

6. The fusion polypeptide of claim 5, wherein the spacer sequence has a length of from 1-10 amino acids.

7. The fusion polypeptide of claim 1, wherein the epitope segment comprises an epitope which is specifically recognized by antibodies occurring in an early or acute phase of a primary infection with said pathogenic organism.

8. The fusion polypeptide of claim 1, wherein the epitope segment comprises and epitope which is specifically recognized by antibodies occurring in a late phase of infection or a past infection with said pathogenic organism.

9. The fusion polypeptide of claim 1, wherein the epitope segment comprises an epitope which is specifically recognized by antibodies occurring in a persisting or recurrent infection with said pathogenic organism.

10. The fusion polypeptide of claim 1, wherein the pathogenic organism is selected from the group consisting of herpes viruses, rubella viruses, hepatitis viruses, paramyxoviruses, *Toxoplasma* organisms, and *Borrelia* organisms.

11. The fusion polypeptide of claim 1, wherein the pathogenic organism is selected from the group consisting of human herpes simplex virus 1 (HHV1), human herpes simplex virus 2 (HHV2), varicella zoster virus (HHV3), Epstein-Barr virus (HHV4/EBV), human cytomegalovirus (HHV5), human herpes viruses 6, 7, and 8, hepatitis A virus (HAV), hepatitis B virus (HBV), hepatitis C virus (HCV), measles virus, and mumps virus.

12. The fusion polypeptide of claim 1, wherein the pathogenic organism is selected from the group consisting of human cytomegalovirus, *Toxoplasma gondii*, and rubella virus.

13. The fusion polypeptide of claim 1, further comprising at least one reporter group.

14. The fusion polypeptide of claim 1, further comprising a biotin coupling group.

15. A multimer comprising a plurality of subunits consisting of the fusion polypeptide of claim 1 associated by non-covalent interaction via the multimerization domain.

16. A nucleic acid encoding a fusion polypeptide comprising at least one multimerization domain and a plurality of copies of an epitope segment from a pathogenic organism, wherein the multimerization domain, which supports multimerization of individual polypeptide molecules, is Skp from *E. coli*, and wherein the epitope segment comprises an epitope which is specifically recognized by antibodies occurring in a specific phase of infection, and wherein the fusion polypeptide is capable of forming a multimer.

17. An expression vector comprising the nucleic acid of claim 16 operatively linked to an expression control sequence.

18. An isolated host cell transfected or transformed with the expression vector of claim 17.

19. A method for producing a fusion polypeptide fusion polypeptide comprising at least one multimerization domain and a plurality of copies of an epitope segment from a pathogenic organism comprising the steps of:
   providing the host cell of claim 18,
   cultivating said host cell under conditions wherein the fusion polypeptide is expressed, and
   recovering said fusion polypeptide, wherein the epitope segment comprises an epitope which his specifically recognized by antibodies occurring in a specific phase of infection.

20. A test reagent kit for detecting an antibody directed against a pathogenic organism in a sample, the kit comprising a fusion polypeptide comprising at least one multimerization domain and a plurality of copies of an epitope segment from a pathogenic organism, wherein the multimerization domain, which supports multimerization of individual polypeptide molecules, is Skp from *E. coli*, and wherein the epitope segment comprises an epitope which is specifically recognized by antibodies occurring in a specific phase of infection, and wherein the fusion polypeptide is capable of forming a multimer.

21. The test reagent of claim 20, wherein said fusion polypeptide is a detection reagent.

22. The test reagent of claim 20, wherein said fusion polypeptide is an interference elimination agent adapted to eliminate binding of undesired antibody types to a test antigen.

* * * * *

UNITED STATES PATENT AND TRADEMARK OFFICE
CERTIFICATE OF CORRECTION

PATENT NO. : 9,261,510 B2
APPLICATION NO. : 12/104751
DATED : February 16, 2016
INVENTOR(S) : Christian Scholz et al.

It is certified that error appears in the above-identified patent and that said Letters Patent is hereby corrected as shown below:

Title Page, item (75), should read:

Inventors: Christian Scholz, Penzberg (DE); Elke Faatz, Huglfing (DE); Peter Schaarschmidt, Uffing (DE); Urban Schmitt, Oberhausen (DE)

Signed and Sealed this
Fourteenth Day of June, 2016

Michelle K. Lee
*Director of the United States Patent and Trademark Office*

SEQUENCE LISTING

```
<160> NUMBER OF SEQ ID NOS: 9

<210> SEQ ID NO 1
<211> LENGTH: 165
<212> TYPE: PRT
<213> ORGANISM: Artificial
<220> FEATURE:
<223> OTHER INFORMATION: SlyD
<220> FEATURE:
<221> NAME/KEY: MISC_FEATURE
<222> LOCATION: (1)..(165)
<223> OTHER INFORMATION: SlyD

<400> SEQUENCE: 1

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp
                165

<210> SEQ ID NO 2
<211> LENGTH: 245
<212> TYPE: PRT
<213> ORGANISM: Artificial
<220> FEATURE:
<223> OTHER INFORMATION: FkpA
<220> FEATURE:
<221> NAME/KEY: MISC_FEATURE
<222> LOCATION: (1)..(245)
<223> OTHER INFORMATION: FkpA (26-270)

<400> SEQUENCE: 2

Ala Glu Ala Ala Lys Pro Ala Thr Ala Ala Asp Ser Lys Ala Ala Phe
1               5                   10                  15

Lys Asn Asp Asp Gln Lys Ser Ala Tyr Ala Leu Gly Ala Ser Leu Gly
            20                  25                  30
```

```
Arg Tyr Met Glu Asn Ser Leu Lys Glu Gln Glu Lys Leu Gly Ile Lys
            35                  40                  45

Leu Asp Lys Asp Gln Leu Ile Ala Gly Val Gln Ala Phe Ala Asp
 50                  55                  60

Lys Ser Lys Leu Ser Asp Gln Glu Ile Glu Gln Thr Leu Gln Ala Phe
 65                  70                  75                  80

Glu Ala Arg Val Lys Ser Ser Ala Gln Ala Lys Met Glu Lys Asp Ala
                85                  90                  95

Ala Asp Asn Glu Ala Lys Gly Lys Glu Tyr Arg Glu Lys Phe Ala Lys
                100                 105                 110

Glu Lys Gly Val Lys Thr Ser Ser Thr Gly Leu Val Tyr Gln Val Val
                115                 120                 125

Glu Ala Gly Lys Gly Glu Ala Pro Lys Asp Ser Asp Thr Val Val Val
            130                 135                 140

Asn Tyr Lys Gly Thr Leu Ile Asp Gly Lys Glu Phe Asp Asn Ser Tyr
145                 150                 155                 160

Thr Arg Gly Glu Pro Leu Ser Phe Arg Leu Asp Gly Val Ile Pro Gly
                165                 170                 175

Trp Thr Glu Gly Leu Lys Asn Ile Lys Lys Gly Gly Lys Ile Lys Leu
                180                 185                 190

Val Ile Pro Pro Glu Leu Ala Tyr Gly Lys Ala Gly Val Pro Gly Ile
            195                 200                 205

Pro Pro Asn Ser Thr Leu Val Phe Asp Val Glu Leu Leu Asp Val Lys
            210                 215                 220

Pro Ala Pro Lys Ala Asp Ala Lys Pro Glu Ala Asp Ala Lys Ala Ala
225                 230                 235                 240

Asp Ser Ala Lys Lys
                245

<210> SEQ ID NO 3
<211> LENGTH: 141
<212> TYPE: PRT
<213> ORGANISM: Artificial
<220> FEATURE:
<223> OTHER INFORMATION: Skp
<220> FEATURE:
<221> NAME/KEY: MISC_FEATURE
<222> LOCATION: (1)..(141)
<223> OTHER INFORMATION: Skp

<400> SEQUENCE: 3

Ala Asp Lys Ile Ala Ile Val Asn Met Gly Ser Leu Phe Gln Gln Val
 1               5                  10                  15

Ala Gln Lys Thr Gly Val Ser Asn Thr Leu Glu Asn Glu Phe Lys Gly
                20                  25                  30

Arg Ala Ser Glu Leu Gln Arg Met Glu Thr Asp Leu Gln Ala Lys Met
            35                  40                  45

Lys Lys Leu Gln Ser Met Lys Ala Gly Ser Asp Arg Thr Lys Leu Glu
 50                  55                  60

Lys Asp Val Met Ala Gln Arg Gln Thr Phe Ala Gln Lys Ala Gln Ala
 65                  70                  75                  80

Phe Glu Gln Asp Arg Ala Arg Arg Ser Asn Glu Glu Arg Gly Lys Leu
                85                  90                  95

Val Thr Arg Ile Gln Thr Ala Val Lys Ser Val Ala Asn Ser Gln Asp
                100                 105                 110

Ile Asp Leu Val Val Asp Ala Asn Ala Val Ala Tyr Asn Ser Ser Asp
```

```
                115                 120                 125
Val Lys Asp Ile Thr Ala Asp Val Leu Lys Gln Val Lys
        130                 135                 140

<210> SEQ ID NO 4
<211> LENGTH: 230
<212> TYPE: PRT
<213> ORGANISM: Artificial
<220> FEATURE:
<223> OTHER INFORMATION: Skp-ppUL32-X1
<220> FEATURE:
<221> NAME/KEY: MISC_FEATURE
<222> LOCATION: (1)..(230)
<223> OTHER INFORMATION: Skp-ppUL32-X1

<400> SEQUENCE: 4

Met Ala Asp Lys Ile Ala Ile Val Asn Met Gly Ser Leu Phe Gln Gln
1               5                   10                  15

Val Ala Gln Lys Thr Gly Val Ser Asn Thr Leu Glu Asn Glu Phe Arg
            20                  25                  30

Gly Arg Ala Ser Glu Leu Gln Arg Met Glu Thr Asp Leu Gln Ala Lys
        35                  40                  45

Met Lys Lys Leu Gln Ser Met Lys Ala Gly Ser Asp Arg Thr Lys Leu
    50                  55                  60

Glu Lys Asp Val Met Ala Gln Arg Gln Thr Phe Ala Gln Lys Ala Gln
65                  70                  75                  80

Ala Phe Glu Gln Asp Arg Ala Arg Arg Ser Asn Glu Glu Arg Gly Lys
                85                  90                  95

Leu Val Thr Arg Ile Gln Thr Ala Val Lys Ser Val Ala Asn Ser Gln
            100                 105                 110

Asp Ile Asp Leu Val Val Asp Ala Asn Ala Val Ala Tyr Asn Ser Ser
        115                 120                 125

Asp Val Lys Asp Ile Thr Ala Asp Val Leu Lys Gln Val Lys Gly Gly
    130                 135                 140

Gly Ser Gly Gly Gly Ser Gly Gly Ser Gly Gly Ser Gly Gly Ser Gly
145                 150                 155                 160

Gly Ser Gly Gly Gly Ala Gly Ala Gly Ala Ile Leu Thr Pro Thr
                165                 170                 175

Pro Val Asn Pro Ser Thr Ala Pro Ala Pro Ala Pro Thr Pro Thr Phe
            180                 185                 190

Ala Gly Thr Gln Thr Pro Val Asn Gly Asn Ser Pro Trp Ala Pro Thr
        195                 200                 205

Ala Pro Leu Pro Gly Asp Met Asn Pro Ala Asn Gly Gly Gly Leu Glu
    210                 215                 220

His His His His His His
225                 230

<210> SEQ ID NO 5
<211> LENGTH: 400
<212> TYPE: PRT
<213> ORGANISM: Artificial
<220> FEATURE:
<223> OTHER INFORMATION: Skp-ppUL32-X4
<220> FEATURE:
<221> NAME/KEY: MISC_FEATURE
<222> LOCATION: (1)..(400)
<223> OTHER INFORMATION: Skp-ppUL32-X4

<400> SEQUENCE: 5

Met Ala Asp Lys Ile Ala Ile Val Asn Met Gly Ser Leu Phe Gln Gln
```

```
  1               5                  10                 15
Val Ala Gln Lys Thr Gly Val Ser Asn Thr Leu Glu Asn Glu Phe Arg
                 20                 25                 30
Gly Arg Ala Ser Glu Leu Gln Arg Met Glu Thr Asp Leu Gln Ala Lys
            35                 40                 45
Met Lys Lys Leu Gln Ser Met Lys Ala Gly Ser Asp Arg Thr Lys Leu
        50                 55                 60
Glu Lys Asp Val Met Ala Gln Arg Gln Thr Phe Ala Gln Lys Ala Gln
 65                 70                 75                 80
Ala Phe Glu Gln Asp Arg Ala Arg Arg Ser Asn Glu Glu Arg Gly Lys
                85                 90                 95
Leu Val Thr Arg Ile Gln Thr Ala Val Lys Ser Val Ala Asn Ser Gln
            100                105                110
Asp Ile Asp Leu Val Asp Ala Asn Ala Val Ala Tyr Asn Ser Ser
        115                120                125
Asp Val Lys Asp Ile Thr Ala Asp Val Leu Lys Gln Val Lys Gly Gly
130                135                140
Gly Ser Gly Gly Gly Ser Gly Gly Ser Gly Gly Ser Gly Gly
145                150                155                160
Gly Ser Gly Gly Gly Ala Gly Ala Gly Ala Ala Ile Leu Thr Pro Thr
                165                170                175
Pro Val Asn Pro Ser Thr Ala Pro Ala Pro Ala Pro Thr Pro Thr Phe
            180                185                190
Ala Gly Thr Gln Thr Pro Val Asn Gly Asn Ser Pro Trp Ala Pro Thr
        195                200                205
Ala Pro Leu Pro Gly Asp Met Asn Pro Ala Asn Gly Gly Gly Ala Gly
210                215                220
Ala Gly Ala Ala Ile Leu Thr Pro Thr Pro Val Asn Pro Ser Thr Ala
225                230                235                240
Pro Ala Pro Ala Pro Thr Phe Ala Gly Thr Gln Thr Pro Val Asn
                245                250                255
Gly Asn Ser Pro Trp Ala Pro Thr Ala Pro Leu Pro Gly Asp Met Asn
            260                265                270
Pro Ala Asn Gly Gly Gly Ala Gly Ala Gly Ala Ala Ile Leu Thr Pro
        275                280                285
Thr Pro Val Asn Pro Ser Thr Ala Pro Ala Pro Ala Pro Thr Pro Thr
290                295                300
Phe Ala Gly Thr Gln Thr Pro Val Asn Gly Asn Ser Pro Trp Ala Pro
305                310                315                320
Thr Ala Pro Leu Pro Gly Asp Met Asn Pro Ala Asn Gly Gly Gly Ala
                325                330                335
Gly Ala Gly Ala Ala Ile Leu Thr Thr Pro Val Asn Pro Ser Thr
            340                345                350
Ala Pro Ala Pro Ala Pro Thr Pro Thr Phe Ala Gly Thr Gln Thr Pro
        355                360                365
Val Asn Gly Asn Ser Pro Trp Ala Pro Thr Ala Pro Leu Pro Gly Asp
370                375                380
Met Asn Pro Ala Asn Gly Gly Gly Leu Glu His His His His His
385                390                395                400
```

<210> SEQ ID NO 6
<211> LENGTH: 226
<212> TYPE: PRT
<213> ORGANISM: Artificial

-continued

```
<220> FEATURE:
<223> OTHER INFORMATION: Skp-pp150-X1
<220> FEATURE:
<221> NAME/KEY: MISC_FEATURE
<222> LOCATION: (1)..(226)
<223> OTHER INFORMATION: Skp-pp150-X1 (pp150 999-1048)

<400> SEQUENCE: 6
```

Met Ala Asp Lys Ile Ala Ile Val Asn Met Gly Ser Leu Phe Gln Gln
 1               5                  10                  15

Val Ala Gln Lys Thr Gly Val Ser Asn Thr Leu Glu Asn Glu Phe Arg
            20                  25                  30

Gly Arg Ala Ser Glu Leu Gln Arg Met Glu Thr Asp Leu Gln Ala Lys
        35                  40                  45

Met Lys Lys Leu Gln Ser Met Lys Ala Gly Ser Asp Arg Thr Lys Leu
    50                  55                  60

Glu Lys Asp Val Met Ala Gln Arg Gln Thr Phe Ala Gln Lys Ala Gln
65                  70                  75                  80

Ala Phe Glu Gln Asp Arg Ala Arg Ser Asn Glu Gly Arg Gly Lys
                85                  90                  95

Leu Val Thr Arg Ile Gln Thr Ala Val Lys Ser Val Ala Asn Ser Gln
            100                 105                 110

Asp Ile Asp Leu Val Val Asp Ala Asn Ala Val Ala Tyr Asn Ser Ser
        115                 120                 125

Asp Val Lys Asp Ile Thr Ala Asp Val Leu Lys Gln Val Lys Gly Gly
    130                 135                 140

Gly Ser Gly Gly Gly Ser Gly Gly Gly Ser Gly Gly Gly Ser Gly Gly
145                 150                 155                 160

Gly Ser Gly Gly Gly Met Lys Thr Val Ala Phe Asp Leu Ser Ser Pro
                165                 170                 175

Gln Lys Ser Gly Thr Gly Pro Gln Pro Gly Ser Ala Gly Met Gly Gly
            180                 185                 190

Ala Lys Thr Pro Ser Asp Ala Val Gln Asn Ile Leu Gln Lys Ile Glu
        195                 200                 205

Lys Ile Lys Asn Thr Glu Glu Gly Gly Gly Leu Glu His His His His
    210                 215                 220

His His
225

```
<210> SEQ ID NO 7
<211> LENGTH: 386
<212> TYPE: PRT
<213> ORGANISM: Artificial
<220> FEATURE:
<223> OTHER INFORMATION: Skp-pp150-X4
<220> FEATURE:
<221> NAME/KEY: MISC_FEATURE
<222> LOCATION: (1)..(386)
<223> OTHER INFORMATION: Skp-pp150-X4 (pp150 999-1048)

<400> SEQUENCE: 7
```

Met Ala Asp Lys Ile Ala Ile Val Asn Met Gly Ser Leu Phe Gln Gln
 1               5                  10                  15

Val Ala Gln Lys Thr Gly Val Ser Asn Thr Leu Glu Asn Glu Phe Arg
            20                  25                  30

Gly Arg Ala Ser Glu Leu Gln Arg Met Glu Thr Asp Leu Gln Ala Lys
        35                  40                  45

Met Lys Lys Leu Gln Ser Met Lys Ala Gly Ser Asp Arg Thr Lys Leu
    50                  55                  60

```
Glu Lys Asp Val Met Ala Gln Arg Gln Thr Phe Ala Gln Lys Ala Gln
 65                  70                  75                  80

Ala Phe Glu Gln Asp Arg Ala Arg Arg Ser Asn Glu Gly Arg Gly Lys
                 85                  90                  95

Leu Val Thr Arg Ile Gln Thr Ala Val Lys Ser Val Ala Asn Ser Gln
            100                 105                 110

Asp Ile Asp Leu Val Val Asp Ala Asn Ala Val Ala Tyr Asn Ser Ser
            115                 120                 125

Asp Val Lys Asp Ile Thr Ala Asp Val Leu Lys Gln Val Lys Gly Gly
            130                 135                 140

Gly Ser Gly Gly Gly Ser Gly Gly Gly Ser Gly Gly Gly Ser Gly Gly
145                 150                 155                 160

Gly Ser Gly Gly Gly Met Lys Thr Val Ala Phe Asp Leu Ser Ser Pro
            165                 170                 175

Gln Lys Ser Gly Thr Gly Pro Gln Pro Gly Ser Ala Gly Met Gly Gly
            180                 185                 190

Ala Lys Thr Pro Ser Asp Ala Val Gln Asn Ile Leu Gln Lys Ile Glu
            195                 200                 205

Lys Ile Lys Asn Thr Glu Glu Gly Gly Met Lys Thr Val Ala Phe
            210                 215                 220

Asp Leu Ser Ser Pro Gln Lys Ser Gly Thr Gly Pro Gln Pro Gly Ser
225                 230                 235                 240

Ala Gly Met Gly Gly Ala Lys Thr Pro Ser Asp Ala Val Gln Asn Ile
            245                 250                 255

Leu Gln Lys Ile Glu Lys Ile Lys Asn Thr Glu Glu Gly Gly Met
            260                 265                 270

Lys Thr Val Ala Phe Asp Leu Ser Ser Pro Gln Lys Ser Gly Thr Gly
            275                 280                 285

Pro Gln Pro Gly Ser Ala Gly Met Gly Gly Ala Lys Thr Pro Ser Asp
            290                 295                 300

Ala Val Gln Asn Ile Leu Gln Lys Ile Glu Lys Ile Lys Asn Thr Glu
305                 310                 315                 320

Glu Gly Gly Gly Met Lys Thr Val Ala Phe Asp Leu Ser Ser Pro Gln
            325                 330                 335

Lys Ser Gly Thr Gly Pro Gln Pro Gly Ser Ala Gly Met Gly Gly Ala
            340                 345                 350

Lys Thr Pro Ser Asp Ala Val Gln Asn Ile Leu Gln Lys Ile Glu Lys
            355                 360                 365

Ile Lys Asn Thr Glu Glu Gly Gly Leu Glu His His His His
            370                 375                 380

His His
385

<210> SEQ ID NO 8
<211> LENGTH: 216
<212> TYPE: PRT
<213> ORGANISM: Artificial
<220> FEATURE:
<223> OTHER INFORMATION: Skp-p52-X1
<220> FEATURE:
<221> NAME/KEY: MISC_FEATURE
<222> LOCATION: (1)..(216)
<223> OTHER INFORMATION: Skp-p52-X1 (p52 254-293)

<400> SEQUENCE: 8

Met Ala Asp Lys Ile Ala Ile Val Asn Met Gly Ser Leu Phe Gln Gln
```

```
  1               5                  10                 15
Val Ala Gln Lys Thr Gly Val Ser Asn Thr Leu Glu Asn Glu Phe Arg
                20                 25                 30

Gly Arg Ala Ser Glu Leu Gln Arg Met Glu Thr Asp Leu Gln Ala Lys
            35                 40                 45

Met Lys Lys Leu Gln Ser Met Lys Ala Gly Ser Asp Arg Thr Lys Leu
 50                 55                 60

Glu Lys Asp Val Met Ala Gln Arg Gln Thr Phe Ala Gln Lys Ala Gln
 65                 70                 75                 80

Ala Phe Glu Gln Asp Arg Ala Arg Arg Ser Asn Glu Glu Arg Gly Lys
                85                 90                 95

Leu Val Thr Arg Ile Gln Thr Ala Val Lys Ser Val Ala Asn Ser Gln
            100                105                110

Asp Ile Asp Leu Val Val Asp Ala Asn Ala Val Ala Tyr Asn Ser Ser
            115                120                125

Asp Val Lys Asp Ile Thr Ala Asp Val Leu Lys Gln Val Lys Gly Gly
        130                135                140

Gly Ser Gly Gly Gly Ser Gly Gly Ser Gly Gly Ser Gly Gly Ser Gly Gly
145                150                155                160

Gly Ser Gly Gly Gly Val Ala Ser Arg Asn Gly Leu Phe Ala Val Glu
            165                170                175

Asn Phe Leu Thr Glu Glu Pro Phe Gln Arg Gly Asp Pro Phe Asp Lys
            180                185                190

Asn Tyr Val Gly Asn Ser Gly Lys Ser Arg Gly Gly Gly Gly Gly
            195                200                205

Leu Glu His His His His His His
        210                215

<210> SEQ ID NO 9
<211> LENGTH: 345
<212> TYPE: PRT
<213> ORGANISM: Artificial
<220> FEATURE:
<223> OTHER INFORMATION: Skp-p52-X4
<220> FEATURE:
<221> NAME/KEY: MISC_FEATURE
<222> LOCATION: (1)..(345)
<223> OTHER INFORMATION: Skp-p52-X4 (p52 254-293)

<400> SEQUENCE: 9

Met Ala Asp Lys Ile Ala Ile Val Asn Met Gly Ser Leu Phe Gln Gln
 1               5                  10                 15

Val Ala Gln Lys Thr Gly Val Ser Asn Thr Leu Glu Asn Glu Phe Arg
                20                 25                 30

Gly Arg Ala Ser Glu Leu Gln Arg Met Glu Thr Asp Leu Gln Ala Lys
            35                 40                 45

Met Lys Lys Leu Gln Ser Met Lys Ala Gly Ser Asp Arg Thr Lys Leu
 50                 55                 60

Glu Lys Asp Val Met Ala Gln Arg Gln Thr Phe Ala Gln Lys Ala Gln
 65                 70                 75                 80

Ala Phe Glu Gln Asp Arg Ala Arg Arg Ser Asn Glu Glu Arg Gly Lys
                85                 90                 95

Leu Val Thr Arg Ile Gln Thr Ala Val Lys Ser Val Ala Asn Ser Gln
            100                105                110

Asp Ile Asp Leu Val Val Asp Ala Asn Ala Val Ala Tyr Asn Ser Ser
            115                120                125
```

-continued

```
Asp Val Lys Asp Ile Thr Ala Asp Val Leu Lys Gln Val Lys Gly Gly
    130             135             140
Gly Ser Gly Gly Gly Ser Gly Gly Gly Ser Gly Gly Gly Ser Gly Gly
145             150             155             160
Gly Ser Gly Gly Gly Val Ala Ser Arg Asn Gly Leu Phe Ala Val Glu
                165             170             175
Asn Phe Leu Thr Glu Glu Pro Phe Gln Arg Gly Asp Pro Phe Asp Lys
            180             185             190
Asn Tyr Val Gly Asn Ser Gly Lys Ser Arg Gly Gly Gly Gly Gly Gly
        195             200             205
Val Ala Ser Arg Asn Gly Leu Phe Ala Val Glu Asn Phe Leu Thr Glu
    210             215             220
Glu Pro Phe Gln Arg Gly Asp Pro Phe Asp Lys Asn Tyr Val Gly Asn
225             230             235             240
Ser Gly Lys Ser Arg Gly Gly Gly Gly Gly Val Ala Ser Arg Asn
                245             250             255
Gly Leu Phe Ala Val Glu Asn Phe Leu Thr Glu Glu Pro Phe Gln Arg
            260             265             270
Gly Asp Pro Phe Asp Lys Asn Tyr Val Gly Asn Ser Gly Lys Ser Arg
        275             280             285
Gly Gly Gly Gly Gly Val Ala Ser Arg Asn Gly Leu Phe Ala Val
    290             295             300
Glu Asn Phe Leu Thr Glu Glu Pro Phe Gln Arg Gly Asp Pro Phe Asp
305             310             315             320
Lys Asn Tyr Val Gly Asn Ser Gly Lys Ser Arg Gly Gly Gly Gly Gly
                325             330             335
Gly Leu Glu His His His His His His
            340             345
```